US012631643B2

(12) United States Patent
Lötvall et al.

(10) Patent No.: US 12,631,643 B2
(45) Date of Patent: May 19, 2026

(54) TISSUE-DERIVED EXTRACELLULAR VESICLES AND THEIR USE AS DIAGNOSTICS

(71) Applicant: Exocure Sweden AB, Gothenburg (SE)

(72) Inventors: Jan Lötvall, Boston, MA (US); Su Chul Jang, Gyeongsangbuk-Do (KR); Rossella Crescitelli, Gothenburg (SE)

(73) Assignee: Exocure Sweden AB, Goeteborg (SE)

( * ) Notice: Subject to any disclaimer, the term of this patent is extended or adjusted under 35 U.S.C. 154(b) by 618 days.

(21) Appl. No.: 17/731,833

(22) Filed: Apr. 28, 2022

(65) Prior Publication Data

US 2022/0334120 A1    Oct. 20, 2022

Related U.S. Application Data

(63) Continuation of application No. 16/494,193, filed as application No. PCT/EP2018/025067 on Mar. 22, 2018, now Pat. No. 11,333,665.

(30) Foreign Application Priority Data

Mar. 23, 2017    (GB) .................................... 1704646

(51) Int. Cl.

| | |
|---|---|
| *G01N 31/00* | (2006.01) |
| *C12N 5/07* | (2010.01) |
| *G01N 33/53* | (2006.01) |
| *G01N 33/564* | (2006.01) |
| *G01N 33/569* | (2006.01) |
| *G01N 33/575* | (2026.01) |
| *G01N 33/5751* | (2026.01) |
| *G01N 33/57545* | (2026.01) |
| *G01N 33/68* | (2006.01) |

(52) U.S. Cl.
CPC ......... *G01N 33/57545* (2026.01); *C12N 5/06* (2013.01); *G01N 33/564* (2013.01); *G01N 33/56977* (2013.01); *G01N 33/5751* (2026.01); *G01N 33/5759* (2026.01); *G01N 33/57595* (2026.01); *G01N 33/6842* (2013.01); *G01N 33/6848* (2013.01)

(58) Field of Classification Search
None
See application file for complete search history.

(56) References Cited

U.S. PATENT DOCUMENTS

| | | | |
|---|---|---|---|
| 9,149,542 B2 | 10/2015 | Gho et al. | |
| 9,220,763 B2 | 12/2015 | Gho et al. | |
| 11,333,665 B2 * | 5/2022 | Lotvall ................ | G01N 33/564 |
| 2008/0207723 A1 | 8/2008 | Kopreski | |
| 2015/0086639 A1 | 3/2015 | Huang | |
| 2015/0218254 A1 | 8/2015 | Sabbadini et al. | |
| 2016/0061842 A1 | 3/2016 | Di Vizio | |
| 2016/0120818 A1 | 5/2016 | Grandi et al. | |

| | | |
|---|---|---|
| 2017/0246288 A1 | 8/2017 | Li et al. |
| 2018/0036240 A1 | 2/2018 | Gho et al. |
| 2018/0296483 A1 | 10/2018 | Gho et al. |
| 2018/0318409 A1 | 11/2018 | Valiante et al. |
| 2020/0249234 A1 | 8/2020 | Lotvall et al. |
| 2022/0080035 A1 | 3/2022 | Park et al. |

FOREIGN PATENT DOCUMENTS

| | | | |
|---|---|---|---|
| EP | 2617413 A2 | 7/2013 | |
| EP | 3251659 A1 | 12/2017 | |
| EP | 2450032 B1 | 9/2018 | |
| WO | WO2009051427 | 4/2009 | |
| WO | WO2009130649 | 10/2009 | |
| WO | WO-2009130649 A2 * | 10/2009 | ............... C12N 1/00 |
| WO | WO2010010983 | 1/2010 | |
| WO | WO2010056337 | 5/2010 | |
| WO | WO2010070124 | 6/2010 | |
| WO | WO2013063439 | 5/2013 | |
| WO | WO2015085096 | 6/2015 | |
| WO | WO2016136372 | 9/2016 | |
| WO | WO2017161010 | 9/2017 | |
| WO | WO2017205810 | 11/2017 | |
| WO | WO2018171947 | 9/2018 | |

OTHER PUBLICATIONS

Romanov et al. (Cell Technologies in Biology and Medicine, No. 3, Nov. 2015, p. 148-154) (Year: 2015).*
Vizio et al. (The American Journal of Pathology, vol. 181, No. 5, Nov. 2012, pp. 1573-1584). (Year: 2012).*
Xavier et al. Molecular Neurodegeneration, published May 23, 2016, vol. 11, No. 41, pp. 1-13. (Year: 2016).*
Corrales et al., (2015) "Direct Activation of STING in the Tumor Microenvironment Leads to Potent and Systemic Tumor Regression and Immunity", Cell Reports, 11(7):1018-1030, XP055771217.
Morein et al. (1994) "Separation of inner and outer membrane vesicles from *Escherichia coli* in self-generating Percoll gradients", Analytical Biochemistry, 216(1):47-51, XP055982965.
Van Der Pol et al. (2015) "Outer membrane vesicles as platform vaccine technology", Biotechnology Journal, 10(11):1689-1706, XP055465407.
Coumans et al., (2017) "Methodological guidelines to study extracellular Vesicles", Circ. Res., 120(10):1632-1648.
Jeppesen et al., (2014) "Quantitative proteomics of fractionated membrane and lumen exosome proteins from isogenic metastatic and nonmetastatic bladder cancer cells reveal differential expression of EMT factors", Proteomics (14)6:699-712.

(Continued)

*Primary Examiner* — Lisa V Cook
(74) *Attorney, Agent, or Firm* — Shweta Chandra; Bozicevic, Field & Francis LLP

(57) ABSTRACT

The present disclosure relates to a method of isolating extracellular vesicles directly from human tissues. The invention further relates to a method of identifying disease and tissue specific membrane proteins on extracellular vesicles by membrane isolation and proteomic analysis. The invention further relates to methods of diagnosing diseases by capturing extracellular vesicles by the use of disease specific membrane proteins from body fluids, and detecting or analyzing molecular signatures (proteome, DNA, and RNA) on captured extracellular vesicles. Moreover, the present invention relates to kits, apparatus and software required for implementing aforementioned methods.

11 Claims, 16 Drawing Sheets

(56) References Cited

OTHER PUBLICATIONS

Karimi et al., (2018) "Detailed analysis of the plasma extracellular vesicle proteome after separation from lipoproteins", Cell. Mol. Life Sci., 75(15):2873-2886.

Mariantonia et al., (2009) "High levels of exosomes expressing CD63 and caveolin-1 in plasma of melanoma patients. e5219", PLOS One, 4(4):1-10.

Matsushita et al., (1989) "Effect of Extracellular pH on the Respiratory Chain and Energetics of Gluconobacter suboxydans", Agricultural and Biological Chemistry,53(11):2895-2902.

Shin et al., (2015) "High-yield isolation of extracellular vesicles using aqueous two-phase system", Scientific Reports, (5)1:1-11.

Tauro et al., (2012) "Two Distinct Populations of Exosomes Are Released from LIM1863 Colon Carcinoma Cell-derived Organoids", Molecular & Cellular Proteomics, 12(3):587-598.

Yoshioka et al., (2014) "Ultra-sensitive liquid biopsy of circulating extracellular vesicles using ExoScreen". Nature Communications, (5)3591:1-8.

U.S. Appl. No. 17/642,140, filed Mar. 10, 2022.

Filip et al., (1973) "Solubilization of the Cytoplasmic Membrane of *Escherichia coli* by the Ionic Detergent Sodium-Lauryl Sarcosinate.", J Bacterial., 115(3):717-722. (Year: 1973).

Zariri et al., (2016) "Meningococcal Outer Membrane Vesicle Composition-Dependent Activation of the Innate", Immune Response, 84(10):3024-3033.

D'Atri et al., (2019) "Nano-Ghosts: mesenchymal stem cells derived nanoparticles as a novel approach for cartilage regeneration." Journal of Extracellular Vesicles, vol. 8, 1 page.

Furman et al., (2013) "Reconstructed Stem Cell Nano ghosts: A Natural Tumor Targeting Platform." Nano Letters, vol. 13, No. 7, pp. 3248-3255.

Go et al., (2018) "Extracellular Vesicle-Mimetic Ghost Nanovesicles for Delivering Anti-Inflammatory Drugs to Mitigate Gram-Negative Bacterial Outer Membrane Vesicle-Induced Systemic Inflammatory Response Syndrome." Advance Healthcare Materials, vol. 8, No. 4.

\* cited by examiner

100

1. No Collagenase and DNase treatment

400

700

900

902

904

1000

1002

1004

1100

1102

1104

TISSUE-DERIVED EXTRACELLULAR VESICLES AND THEIR USE AS DIAGNOSTICS

CROSS REFERENCE TO RELATED APPLICATIONS

This application is a continuation of Ser. No. 16/494,193 filed on Sep. 13, 2019, issued as U.S. Pat. No. 11,333,665; which is a national phase of PCT/EP2018/025067 filed on Mar. 22, 2018; which claims priority benefit to GB Provisional Application No. 1704646.7, filed Mar. 23, 2017 which is herein incorporated by reference in its entirety.

TECHNICAL FIELD

The present disclosure relates to apparatus and methods for extracellular vesicles-based diagnosis of diseases, in particular apparatus and methods for identifying membrane proteins on extracellular vesicles which are specific for diseases and diagnosing diseases by using them. Moreover, the present disclosure relates to methods of isolating extracellular vesicles from tissues and identifying membrane proteins by membrane isolation, so called membrane proteomics. Furthermore, the present disclosure also relates to computer program products comprising non-transitory (namely non-transient) computer-readable storage media having computer-readable instructions stored thereon, the computer-readable instructions being executable by a computerized device comprising processing hardware to execute the aforesaid methods.

BACKGROUND

Extracellular vesicles are nano-sized vesicles (40 nm to 1000 nm in diameter) with a lipid bi-layer membrane and are known to be released by many cells in the human body; extracellular vesicles include, for example, exosomes, ectosomes, microvesicles and apoptotic bodies. Such extracellular vesicles are operable to mediate intercellular communication by either activating surface receptors of recipient cells or by transferring cargo proteins, nucleic acids (DNAs, mRNAs, siRNAs, miRNAs, and small non-coding RNAs), or lipids to recipient cells. One of the most attractive considerations for extracellular vesicles is that a cargo of these extracellular vesicles is protected from extracellular enzymes and an immune system by a lipid membrane bilayer.

Extracellular vesicles have been found in many body fluids including blood (plasma and serum), urine, ejaculate, saliva, cerebrospinal fluid, ascites, synovial fluid, bronchoalveolar lavage, pleural effusion, amniotic fluid, sweats, feces, cystic fluids, tears and breast milk, and they are considered to carry signatures of the cells that produce them. This means that extracellular vesicles have a significant potential as functioning as diagnostic markers when seeking to detect diseases. Several extracellular vesicular markers have been proposed for use in cancer diagnosis, including glypican-1 protein, EpCAM protein, KRAS-mutated DNA, and oncogenic mRNA and microRNAs.

Several cell types including reticulocytes, dendritic cells, B cells, T cells, mast cells, epithelial cells, and embryonic cells are known to be capable of releasing exosomes, however their increased amount in the peripheral circulation appears to be unique to pregnancy and cancer. Furthermore, the primary source of circulating exosomes may be associated with tumors. Tumor patients have been found to have very high levels of tumor derived exosomes in plasma, ascites and pleural effusions.

To date, extracellular vesicular biomarker candidates have initially been identified in extracellular vesicles from a cell line, and have in some cases been proposed to be valid also for clinical diagnosis, but are often not detectable in real clinical diseases. Thus, such approaches are not considered to be valid ways to identify extracellular vesicular biomarkers for human disease. Therefore, any molecular signature of extracellular vesicles from human diseased tissue still remains to be described.

SUMMARY

It is an object of the present disclosure to provide a new methodology for isolating extracellular vesicles from human tissues and identifying membrane and other extracellular vesicular molecular signatures as biomarker candidates.

A further objective of the present disclosure is to use the membrane proteins, and other molecular signatures, in diagnosis of diseases.

These and other objects, which are evident to the skilled person from the present disclosure, are met by the different aspects of the invention as claimed in the appended claims and as generally disclosed herein.

According to first aspect, the invention is realized by a method for isolating extracellular vesicles and identifying membrane proteins comprising:

(a) providing human tissues;

(b) chopping the human tissues to make a plurality of pieces of the human tissue;

(c) isolating the extracellular vesicles from the chopped pieces of human tissue;

(d) treating the extracellular vesicles with an aqueous solution, wherein the aqueous solution has a pH in a range of 9 to 14 to obtain membranes;

(e) isolating the membranes;

(f) identifying proteins on the membranes by employing mass spectrometry to identify tissue and/or disease-specific membrane proteins; and (g) isolating extracellular vesicles with such specific membrane proteins to identify at least one of:

i. their disease-specific proteome;

ii. their disease-related RNA cargo; and iii. their disease-related DNA cargo.

Optionally, the method further comprises a step:

(h) incubating with enzymes to release the extracellular vesicles from a tissue matrix, wherein the step h is performed concomitantly after the step (a), (b), or (c).

The above defined method provides methods to isolate the extracellular vesicles from human tissues and to identify the membrane protein signatures for further analysis and biomarker discovery. All cells in vivo produce the extracellular vesicles, and those extracellular vesicles are to a great extent entrapped in extracellular matrix of tissues. The released vesicles from any cell, or from any tissue, include a cloud of vesicles with different content, membrane molecules and with cellular origin. This makes the extracellular vesicles attractive biomarker sources. Current extracellular vesicles-based markers are identified from cultured cells, not from actual in vivo organ environment. Through the present invention, extracellular vesicles are isolated directly from human tissues, which are more relevant and realistic than cell culture-derived extracellular vesicles.

Optionally, the human tissues of steps (a) and (b) are obtained from a human body including tumors or diseased tissues. Further, the human tissues are derived from at least one of: liver, brain, kidney, heart, lung, skin, stomach, intestines, lymph nodes, bone marrow, adipose tissue, central and peripheral neural tissues, endocrine organs and muscles.

Optionally, isolating the membranes at the step (e) includes ultracentrifugation.

Optionally, the enzymes of the step (h) are one enzyme or combination of enzymes that are chosen from proteases including matrix metalloproteinase, collagenases, and papain and nucleases including DNase, RNase, and Benzonase.

Optionally, the RNA and DNA cargo of the step g are mutated RNAs or DNAs, or non-mutated profiles of RNA and/or DNA sequences/genes.

According to an embodiment, the invention is realized by a method of diagnosing diseases using tissue or disease-specific membrane proteins on extracellular vesicles from body fluids, characterized in that the method comprises steps of:

(a) isolating extracellular vesicles and identifying membrane proteins using a method of first aspect;

(b) capturing extracellular vesicles by using an epitope specific binder against the tissue or disease-specific membrane proteins; and (c) detecting extracellular vesicles by using an epitope specific binder against the tissue or disease-specific membrane proteins, or a combination of proteins.

Alternatively, the invention is realized by a method of diagnosing diseases using tissue or disease-specific membrane proteins on extracellular vesicles obtained from body fluids, characterized in that the method comprises steps of:

(a) isolating extracellular vesicles and identifying membrane proteins using a method of first aspect;

(b) capturing extracellular vesicles by using an epitope-specific binder against the tissue or disease-specific membrane proteins; and (c) detecting nucleic acids on or in the captured extracellular vesicles.

Alternatively, the invention is realized by a method of diagnosing diseases using tissue and disease-specific membrane proteins on extracellular vesicles from body fluids, characterized in that the method comprises steps of:

(a) isolating extracellular vesicles and identifying membrane proteins using a method of first aspect;

(b) adding an epitope-specific binder against a tissue or disease-specific membrane protein and a lipid-biotin conjugate to sample; and (c) detecting a tissue-specific membrane protein by using alpha LISA donor and acceptor beads.

Optionally, the body fluids are blood (plasma and serum), urine, ejaculate, saliva, cerebrospinal fluid, ascites, synovial fluid, sputum, pleural effusion, amniotic fluid, sweats, feces, cystic fluids, tears and breast milk, or lavage fluids from different body cavities such as lung, pleural cavity, stomach, small intestine, colon, nose, urinary bladder or the peritoneal cavity. More optionally, the epitope specific binder is an antibody, an aptamer, or a peptide.

Optionally, the tissue or disease-specific membrane protein is a plasma membrane protein. More optionally, the plasma membrane protein is HLA-DR protein.

Optionally, the tissue or disease-specific membrane protein is a mitochondrial membrane protein. More optionally, the mitochondrial membrane protein is MTCO2 and/or COX6C proteins.

Optionally, the tissue or disease specific membrane protein is an endoplasmic reticulum membrane protein that includes at least one of Erlin-2 or RPN1 proteins.

Optionally, the diseases are cancers and/or inflammatory diseases. More optionally, the nucleic acids are DNAs, mRNAs, miRNAs, ribosomal RNAs, and small non-coding RNAs and any other full length or fragment of RNAs or DNAs, including mutation-specific molecules.

Alternatively, the lipid-biotin conjugate is a cholesterol-polyethylene glycol (PEG)-biotin.

According to a second aspect, the invention is realized by a kit for capturing extracellular vesicles and detecting disease-associated markers, characterized in that the kit comprises:

(a) an epitope specific binder against tissue or disease-specific membrane proteins: and (b) at least one disease-associated marker detection agent.

Optionally, the tissue or disease-specific membrane protein is a plasma membrane protein, preferably HLA-DR protein.

Optionally, the tissue or disease-specific membrane protein is a mitochondrial membrane protein. More optionally, the mitochondrial membrane protein is MTCO2 and/or COX6C proteins. More optionally, the tissue or disease specific membrane protein is an endoplasmic reticulum membrane protein that includes at least one of Erlin-2 or RPN1 proteins. Optionally, the kit is adapted for use in any of the methods of isolating extracellular vesicles and identifying membrane proteins and/or diagnosing diseases using tissue or disease-specific membrane proteins on extracellular vesicles from body fluids.

According to third aspect, the invention is realized by an apparatus for implementing the methods of isolating extracellular vesicles and identifying membrane proteins and/or diagnosing diseases using tissue or disease-specific membrane proteins on extracellular vesicles from body fluids.

According to fourth aspect, the invention is realized by a computer program product comprising non-transitory (namely non-transient) computer-readable storage media having computer-readable instructions stored thereon, the computer-readable instructions being executable by a computerized device comprising processing hardware to execute any of the method of isolating extracellular vesicles and identifying membrane proteins and/or diagnosing diseases using tissue or disease-specific membrane proteins on extracellular vesicles from body fluids.

It will be appreciated that features of the invention are susceptible to being combined in various combinations without departing from the scope of the invention as defined by the appended claims.

A better understanding of the present invention may be obtained through the following examples which are set forth to illustrate, but are not to be construed as limiting the present invention.

BRIEF DESCRIPTION OF THE DRAWINGS

Embodiments of the present disclosure will be more fully understood from examples described herein below and the accompanying drawings, which is given by way of illustration only, and thus are not limitative of the present invention, and wherein.

LIST OF ABBREVIATIONS

Abbreviation Meaning

Figure 1:
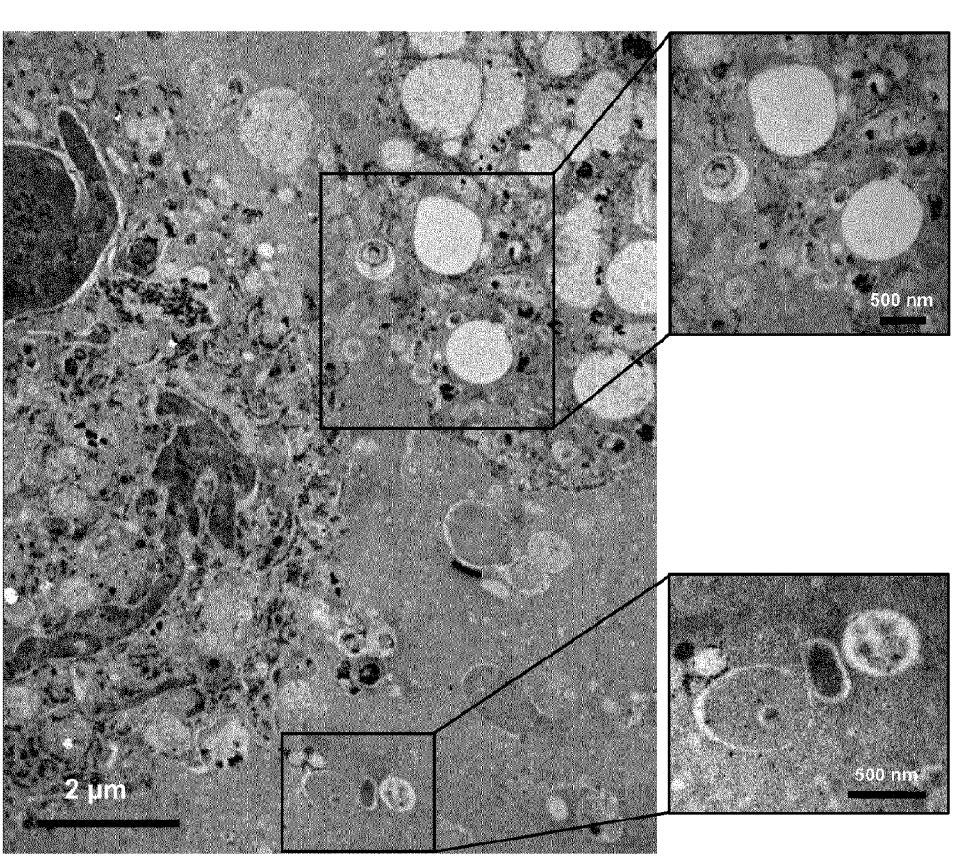
FIG. 1 is an image wherein there is observed a presence of extracellular vesicles in interstitial space of a melanoma metastatic tissue, as revealed by electron microscopy.

PBS Phosphate-buffered saline
EDTA Ethylenediaminetetraacetic acid
BSA Bovine serum albumin
MTCO2 Mitochondrially encoded cytochrome c oxidase II
SLC25A22 Solute Carrier Family 25 Member 22
COX6C Cytochrome c oxidase subunit 6C
EpCAM Epithelial cell adhesion molecule
HLA-DR Human Leukocyte Antigen-antigen D Related
HRP Horseradish peroxidase
ELISA Enzyme-linked immunosorbent assay
FACS Fluorescence-activated cell sorting
LC-MS/MS Liquid chromatography tandem-mass spectrometry
LFQ Label free quantification
M Molar, mol/liter
mM Millimolar, millimol/liter
nm Nanometer
ml Milliliter
DNA Deoxyribonucleic acid
RNA Ribonucleic acid
mRNA Messenger RNA
miRNA Micro RNA
siRNA Small interfering RNA
HMC1 Human mast cell line-1
MSC Mesenchymal stem cell
MeT Metastatic tissue
RPMI Roswell Park Memorial Institute
ROC Receiver operating characteristic
AUC Area under curve
H hour Definitions As used herein, the following terms shall have the following meanings:

As used herein, the term "extracellular vesicle" means a vesicle released by a cell. Examples of "extracellular vesicles" include exosomes, ectosomes, microvesicles, prostasomes, oncosomes, and apoptotic bodies.

The term "membrane" means biological membranes, i.e. the outer coverings of cells and organelles that allow passage of certain compounds. When the term "membrane" is used as a noun herein, it typically refers to an extracellular vesicle or organelle which encloses an intravesicular or organellar content and which has been opened to provide a non-enclosing form of the extracellular vesicle or organelle, i.e. a membrane form. Such membrane may originate from the outer Cell membrane, the Golgi-apparatus, the Endoplasmic reticulum, the nucleus or mitochondria.

The term "cancer" refers to a group of different diseases, which are characterized by unregulated cell growth and infiltration to neighboring tissues due to the disruption of programmed cell death. A target to be diagnosed according to the present invention may be selected from a cancers selected from the group consisting of, but not limited to, carcinoma originating from epithelial cells, such as lung cancer, larynx cancer, stomach cancer, large intestine/rectal cancer, liver cancer, gallbladder cancer, pancreatic cancer, breast cancer, uterine cervical cancer, prostate cancer, kidney cancer, skin cancer, or non-epithelial malignancies such as malignant melanoma, sarcoma originating from connective tissue cells, such as bone cancer, muscle cancer, adipose tissue sarcoma, mesothelioma, etc., blood cancer originating from hematopoietic cells or lymphatic system, such as leukemia, lymphoma, multiple myeloma, etc., and neuroma, neuroblastoma, medulloblastoma or any other tumor originating in peripheral or central nervous system.

The term "inflammatory diseases," as used herein, refers to a syndrome or symptom including edema, resulting from an abnormal accumulation of body fluid in tissues, congestion due to vascular dilation, increased heat by pyrogen and vasodilatation, and pain induced by arachidonic acid metabolites. Inflammation may be classified as acute, sub-acute, and chronic inflammation according to time, and as infectious, allergic, auto-immune, toxic, metabolic and traumatic inflammatory diseases according to pathophysiological conditions. A target to be diagnosed according to the present invention may be selected from the group consisting of, but not limited to, respiratory inflammatory diseases such as rhinitis, sinusitis, otitis media, rhinopharyngitis, laryngitis, bronchitis, asthma, chronic obstructive pulmonary disease, emphysema, bronchiectasis, bronchiolitis, pneumonia, pulmonary fibrosis, etc., inflammatory diseases of the digestive system such as stomatitis, esophagitis, gastritis, peptic ulcer, irritable bowel syndrome, ulcerative colitis, cholecystitis, cholangitis, pancreatitis, hepatitis, etc., skin inflammation such as atopic dermatitis, psoriasis, etc., cardiovascular inflammatory diseases such as endocarditis, myocarditis, pericarditis, vasculitis, arteriosclerosis, sepsis, etc., inflammatory diseases of the endocrine system, such as thyroiditis, parathyroiditis, diabetes, etc., inflammatory diseases of the urogenital system such as nephritis, nephropathy, interstitial nephritis, orchitis, oophoritis, endometritis, vaginosis, etc., inflammatory diseases of the musculoskeletal system, such as rheumatoid arthritis, spondylarthritis, ostarthritis, gout, systemic lupus erythematosusethematosus, systemic sclerosis, myopathy, Sjogren syndrome, Behcet's disease, antiphospholipid syndrome, etc., inflammatory diseases of the Neuropsychiatric system, such as vascular dementia, Alzheimer's disease, degenerative brain diseases, depression, schizophrenia, and etc.

The terms "cell media", "culture media" and/or "cell culture media" as used herein refer to a culture media used for preserving or culturing Melanoma metastatic tissues, cells and/or cell lines obtained from patient during surgery. The culture media include all supplements required for culturing and preservation of melanoma and/or carcinoma cell lines. The culture media may not include fetal bovine serum. For example, if the sample is a solid sample, cells from the sample can be cultured and exosome product is induced. In some embodiments, the sample is ascites fluid from a subject, e.g., ascites fluid from a human subject with ovarian cancer; cell culture media supernatant from a human primary melanoma cell line; cell culture mediasupernatant from a human primary colon cancer cell line; or murine macrophage, e.g., murine macrophage infected with tuberculosis. The culture media may be an ordinary medium, or may also be liquid nitrogen based medium. The liquid medium can be isotonic, hypotonic, or hypertonic. In certain embodiments, the liquid medium contains a buffer and/or at least one salt or a combination of salts. Buffers can maintain pH within a particular range, for example, between 1 and 12, and are also referred to as pH stabilizing agents.

The term "membrane carrier" as used herein refers to membrane proteins that use electrochemical gradients to move selective chemical substrates across lipid bilayers. The membrane carriers may be deep membrane carriers. Furthermore, the membrane carriers may include but not limited to ions and small soluble organic molecules and/or lipid soluble substrates. The membrane proteins that may candidates to be biomarkers are listed in Table-1.

The term "apoptoticbody" as used herein refers to degenerate basal epidermal cells. The apoptotic bodies may include but not limited to colloid, hyaline, filamentous and/or civattebodies. Furthermore, the apoptotic bodies may be round, shrunken, homogeneous, eosinophilic bodies in the stratum basale.

DETAILED DESCRIPTION

The practice of the embodiments described in further detail below will employ, unless otherwise indicated, conventional methods of diagnostics, molecular biology, cell biology, biochemistry and immunology within the skill of the art. Such techniques are explained fully in the literature.

It is appreciated that certain features of the invention, which are for clarity described in the context of separate embodiments may also be provided in combination in a single embodiment. Conversely various features of the invention, which are for brevity, described in the context of a single embodiment, may also be provided separately and/or in any suitable sub-combination.

The methodology for isolating extracellular vesicles from human tissues and identifying membrane and other extracellular vesicular molecular signatures as biomarker candidates of the present disclosure is a method of isolating extracellular vesicles and identifying membrane proteins, the method including steps of providing human tissues; chopping the human tissues to make a plurality of pieces of the human tissue; isolating the extracellular vesicles from the chopped pieces of human tissue; treating the extracellular vesicles with an aqueous solution, wherein the aqueous solution has a pH in a range of 9 to 14 to obtain membranes;

isolating the membranes; identifying proteins on the membranes by employing mass spectrometry to identify tissue and/or disease-specific membrane proteins; and isolating extracellular vesicles with such specific membrane proteins to identify at least one of their disease-specific proteome, their disease-related RNA cargo and their disease-related DNA cargo.

In an embodiment, the method of isolating extracellular vesicles and identifying membrane proteins may include incubating the specific membrane proteins with enzymes to release the extracellular vesicles from a matrix just after providing the human tissues.

In another embodiment, the method of isolating extracellular vesicles and identifying membrane proteins may include incubating the specific membrane proteins with enzymes to release the extracellular vesicles from a matrix just after chopping the human tissues.

In yet another embodiment, the method of isolating extracellular vesicles and identifying membrane proteins may include incubating the specific membrane proteins with enzymes to release the extracellular vesicles from a matrix just after isolating the extracellular vesicles from the chopped pieces of human tissue.

In an embodiment, the human tissues may include tumor or diseased tissues and there may be no particular limitation on selection of human tissues. In an exemplary embodiment, the human tissues may be derived from but not limited to liver, brain, kidney, heart, lung, skin, stomach, intestines, lymph nodes, bone marrow, adipose tissue and muscles.

In an embodiment, isolating the membranes from the extracellular vesicles may include ultracentrifugation. For example, the membrane may be isolated using density gradient ultracentrifugation.

In an embodiment, the enzymes used in incubation for releasing the extracellular vesicles from the matrix may include enzyme or combination of enzymes chosen from proteases including matrix metalloproteinase, collagenases, and papain and nucleases including DNase, RNase, and Benzonase.

In another embodiment, identified disease-related RNA cargo or DNA cargo of the specific membrane proteins of the isolated extracellular vesicles may be mutated RNAs or DNAs.

The method of diagnosing diseases of the present disclosure is a method of diagnosing diseases using tissue or disease-specific membrane proteins on extracellular vesicles from body fluids. The method includes steps of isolating extracellular vesicles and identifying membrane proteins, capturing extracellular vesicles by using an epitope specific binder against the tissue or disease-specific membrane proteins and detecting extracellular vesicles by using an epitope specific binder against the tissue or disease-specific membrane proteins, or a combination of proteins.

The method further includes steps of adding an epitope-specific binder against a tissue or disease-specific membrane protein and a lipid-biotin conjugate to sample and detecting a tissue-specific membrane protein by using alpha capturing extracellular vesicles by using an epitope specific binder against the tissue or disease-specific membrane proteins donor and acceptor beads.

In an embodiment, the method may include isolating the extracellular vesicles from body fluids for providing the human tissues.

In an embodiment, the body fluids may include but not limited to blood (plasma and serum), urine, ejaculate, saliva, cerebrospinal fluid, ascites, synovial fluid, sputum, pleural effusion, amniotic fluid, sweats, feces, cystic fluids, tears and breast milk, or lavage fluids from different body cavities such as lung, pleural cavity, stomach, small intestine, colon, nose, urinary bladder or the peritoneal cavity.

In an embodiment, the epitope specific binder may be an antibody, an aptamer, and/or a peptide.

In another embodiment, the tissue or disease-specific membrane protein may be a plasma membrane protein. For example, the plasma membrane protein may be HLA-DR protein and the tissue or disease-specific membrane protein may be a mitochondrial membrane protein. In an exemplary embodiment, the mitochondrial membrane protein may be MTCO2 and/or COX6C proteins.

In another embodiment, the tissue or disease specific membrane protein may be an endoplasmic reticulum membrane protein. In an exemplary embodiment, the endoplasmic reticulum membrane proteins may be Erlin-2 and/or RPN1 proteins.

In an embodiment, the diseases may be cancers and/or inflammatory diseases, as described above.

In another embodiment, the nucleic acids may include but not limited to DNAs, mRNAs, miRNAs, ribosomal RNAs, and small non-coding RNAs and any other full length or fragment of RNAs or DNAs, including mutation-specific molecules.

In an exemplary embodiment, the lipid-biotin conjugate may be a cholesterol-polyethylene glycol (PEG)-biotin.

The kit of the present disclosure for capturing extracellular vesicles is a kit for capturing extracellular vesicles and detecting disease-associated markers. The kit includes an epitope specific binder for tissue or disease-specific membrane proteins and at least one disease-associated marker detection agent.

In an embodiment, the tissue or disease-specific membrane protein may be a plasma membrane protein. For example, the plasma membrane protein may be a HLA-DR protein.

In another embodiment, the tissue or disease-specific membrane protein may be a mitochondrial membrane protein. For example, the mitochondrial membrane protein may be MTCO2 and/or COX6C proteins.

In yet another embodiment, the tissue or disease specific membrane protein may be an endoplasmic reticulum membrane protein. For example, the endoplasmic reticulum membrane protein may be Erlin-2 and/or RPN1 proteins.

In an embodiment, the kit may be adapted to be used in the method of isolating extracellular vesicles and identifying membrane proteins.

In another embodiment, the kit may be adapted to be used in the method of diagnosing diseases using tissue or disease-specific membrane proteins on extracellular vesicles from body fluids.

The present disclosure provides an apparatus for implementing the method of isolating extracellular vesicles and identifying membrane proteins and the method of diagnosing diseases using tissue or disease-specific membrane proteins on extracellular vesicles from body fluids.

The present disclosure further provides a computer program product including non-transitory computer-readable storage media having computer-readable instructions stored thereon, the computer-readable instructions being executable by a computerized device comprising processing hardware to execute the method of isolating extracellular vesicles and identifying membrane proteins and the method of diagnosing diseases using tissue or disease-specific membrane proteins on extracellular vesicles from body fluids, described herein above.

The invention is now described by means of non-limiting examples.

EXAMPLES

In the following, the examples of the present disclosure will be described. The examples concern methods of processing sample material, as well as apparatus that is operable to implement the methods of processing sample material; for example, the apparatus is implemented in a form of a sample processing kit.

Example 1: Presence of Extracellular Vesicles in Interstitial Space of a Tumor Tissue Revealed by Electron Microscopy Materials and Method A method developed relates to a study that was approved by the Regional Ethical Review Board at the University of Gothenburg (096-12) and all participants provided a written informed consent. The method includes obtaining melanoma metastatic tissues from patients (i.e. participants) during surgery. Thereafter, the method includes preserving the melanoma metastatic tissues in complete cell media (without fetal bovine serum) at a temperature of 4° C., until extracellular vesicle isolation is achieved. Thereafter, the method includes placing the samples of the tissue in 150 μm deep membrane carriers (Leica Microsystems) filled with 20% BSA in PBS followed by high pressure freezing using EMPactI machine (Leica Microsystems). Thereafter, the method includes applying a freeze substitution protocol, as follows: 2% uranyl acetate in dehydrated acetone for 1 h. The method includes increasing the temperature by 3° C. per hour up to −50° C. Thereafter, the method includes washing the samples two times with dehydrated acetone and then infiltrating with increasing concentrations of HM20 (3:1, 2:1, 1:1, 1:2, 1:3 acetone:HM20) followed with 3 changes with HM20. Thereafter, the method includes polymerizing the samples using UV light for 48 h. Thereafter, the method includes cutting thin sections (70 nm) by using a Leica UC6 ultramicrotome (Leica Microsystems). Thereafter, the method includes contrasting the sections using 2% uranyl acetate for 4 min and lead citrate for 2 min.
Results:

The method provides a result, wherein melanin (stained as black) is clearly visible inside melanoma cells; in a practical use of the method, two melanoma cells are well recognized by their cell membrane 100 as shown in FIG. 1. Moreover, in FIG. 1, in the interstitial space of tissues, small size of vesicular structures with various size and morphology are found. This result shows that the interstitial space is abundant with many extracellular vesicles.

Example 2: Isolation of Extracellular Vesicles by Three Different Protocols

Figure 2:
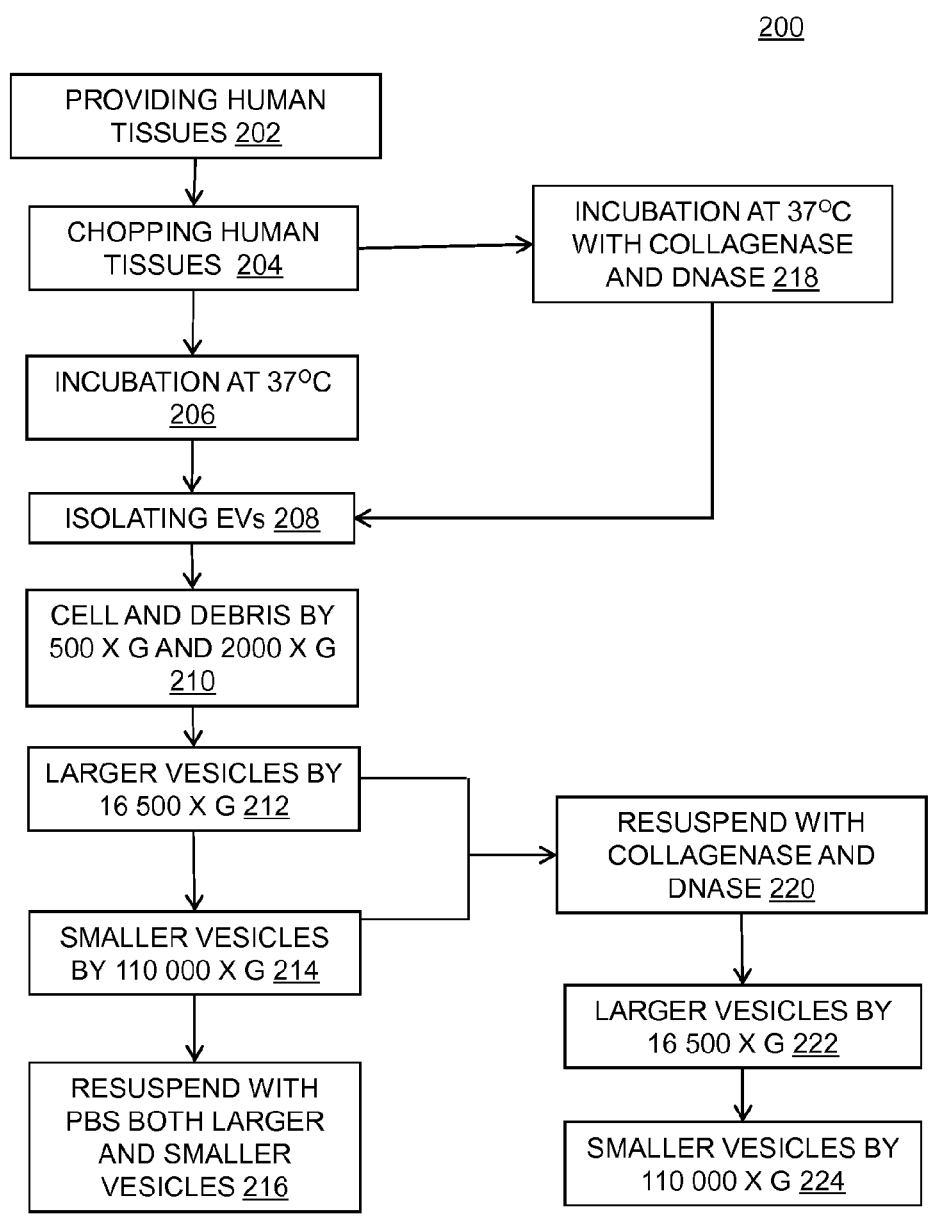
FIG. 2 is a schematic illustration of three different protocols for isolating the extracellular vesicles from melanoma metastatic tissues.
Figure 3A:
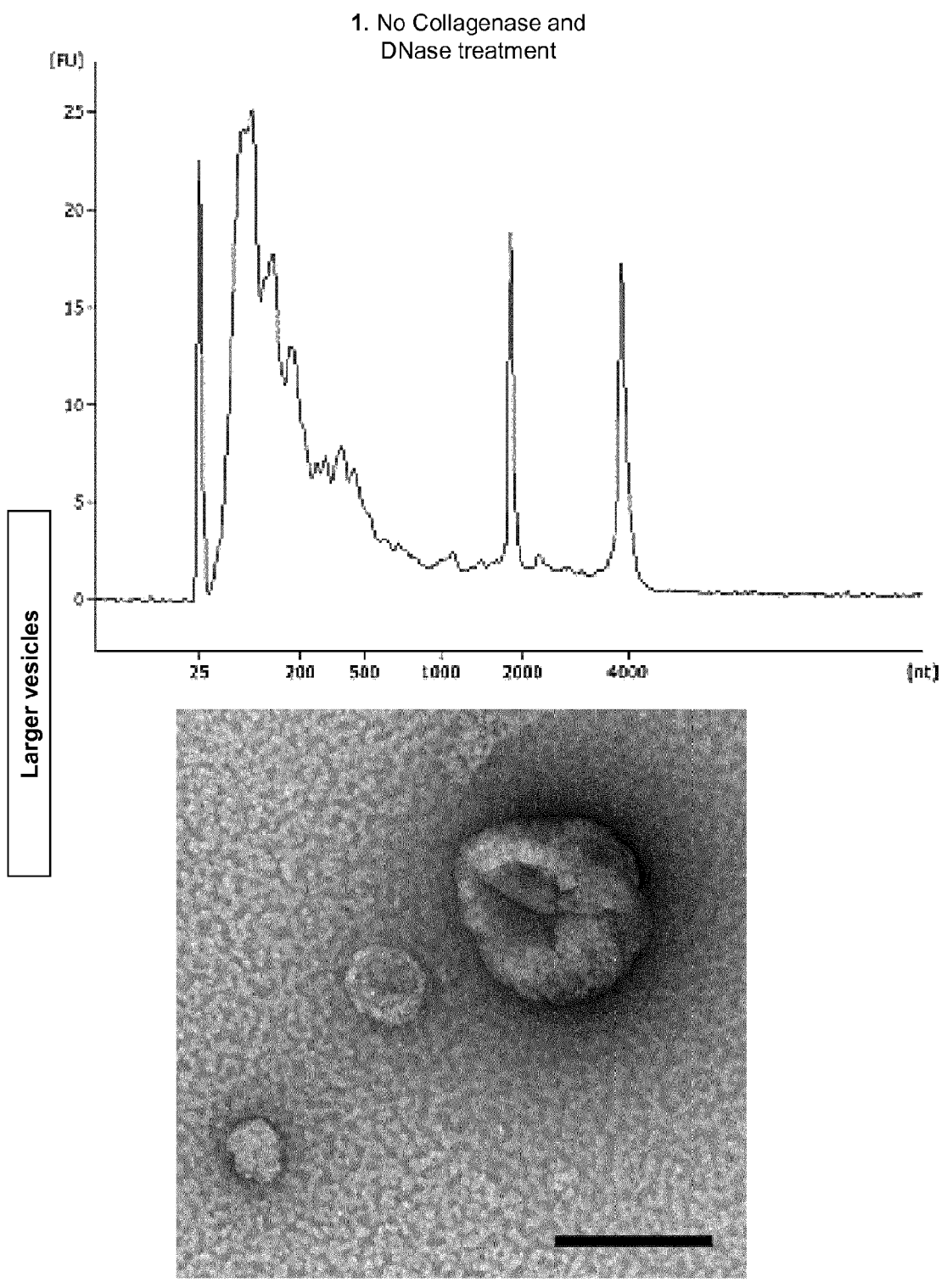
FIGS. 3A-3F depict an RNA profile and morphology of extracellular vesicles isolated by three different protocols.
Figure 3B:
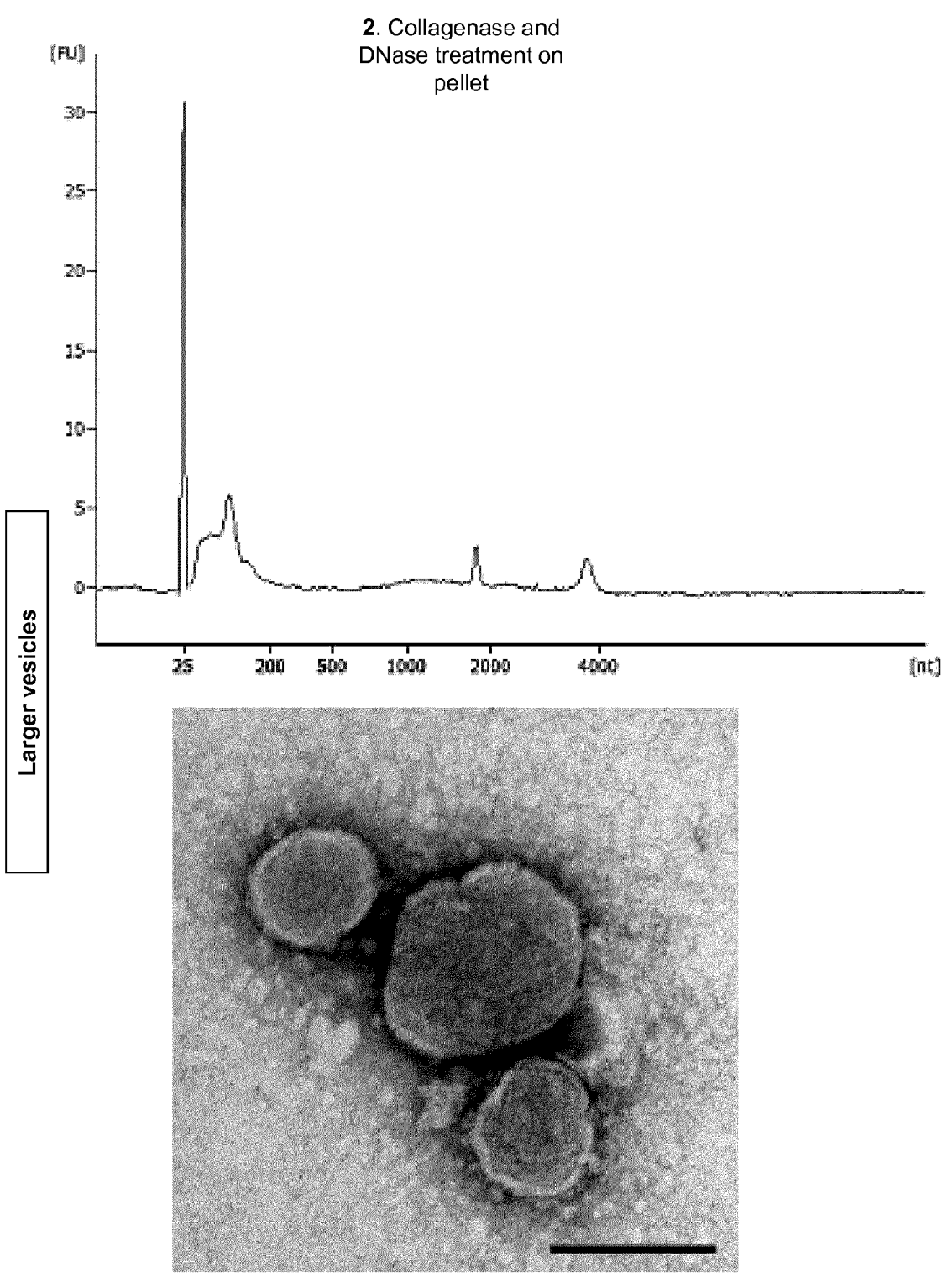
Figure 3C:
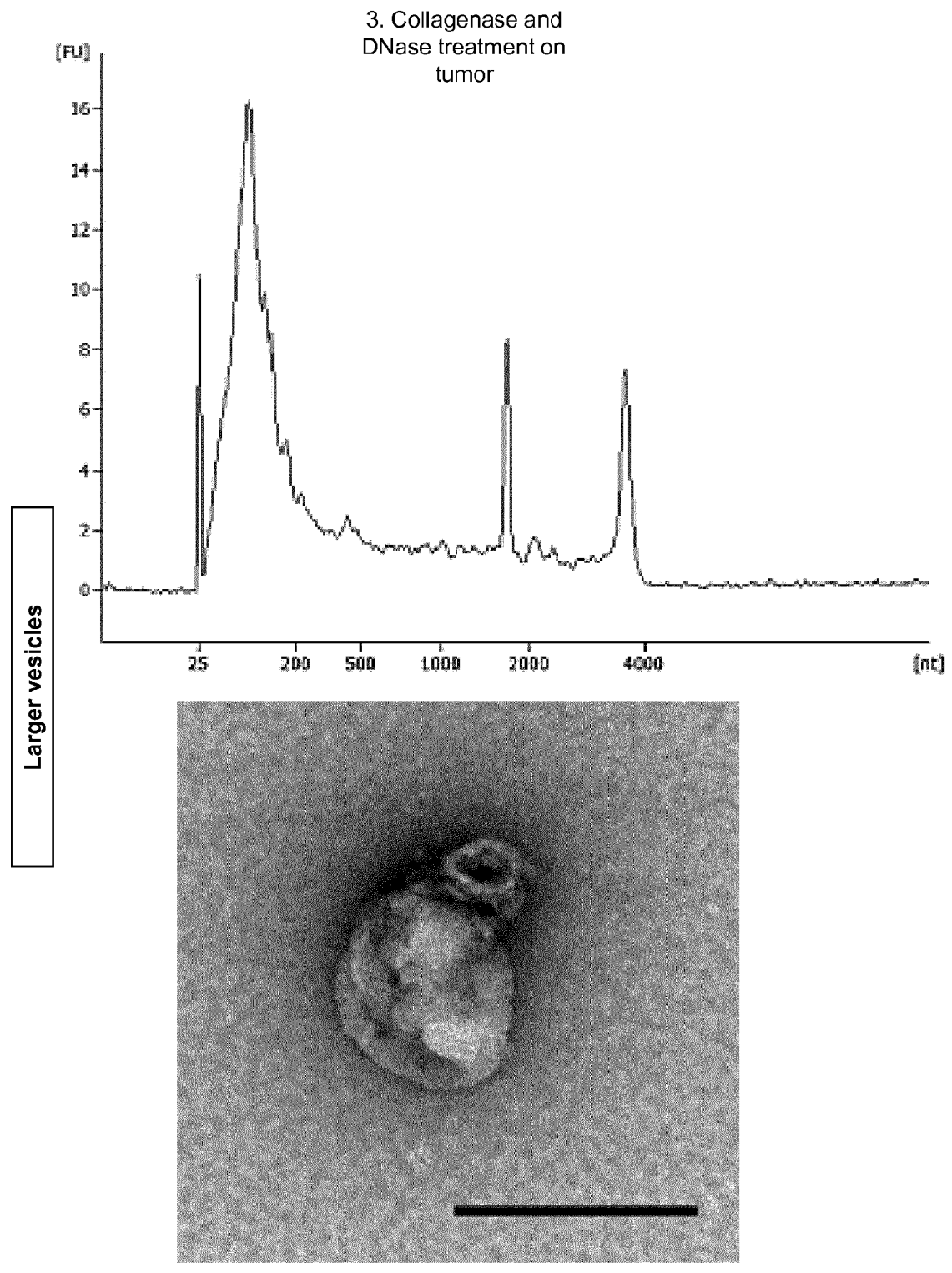
Figure 3D:
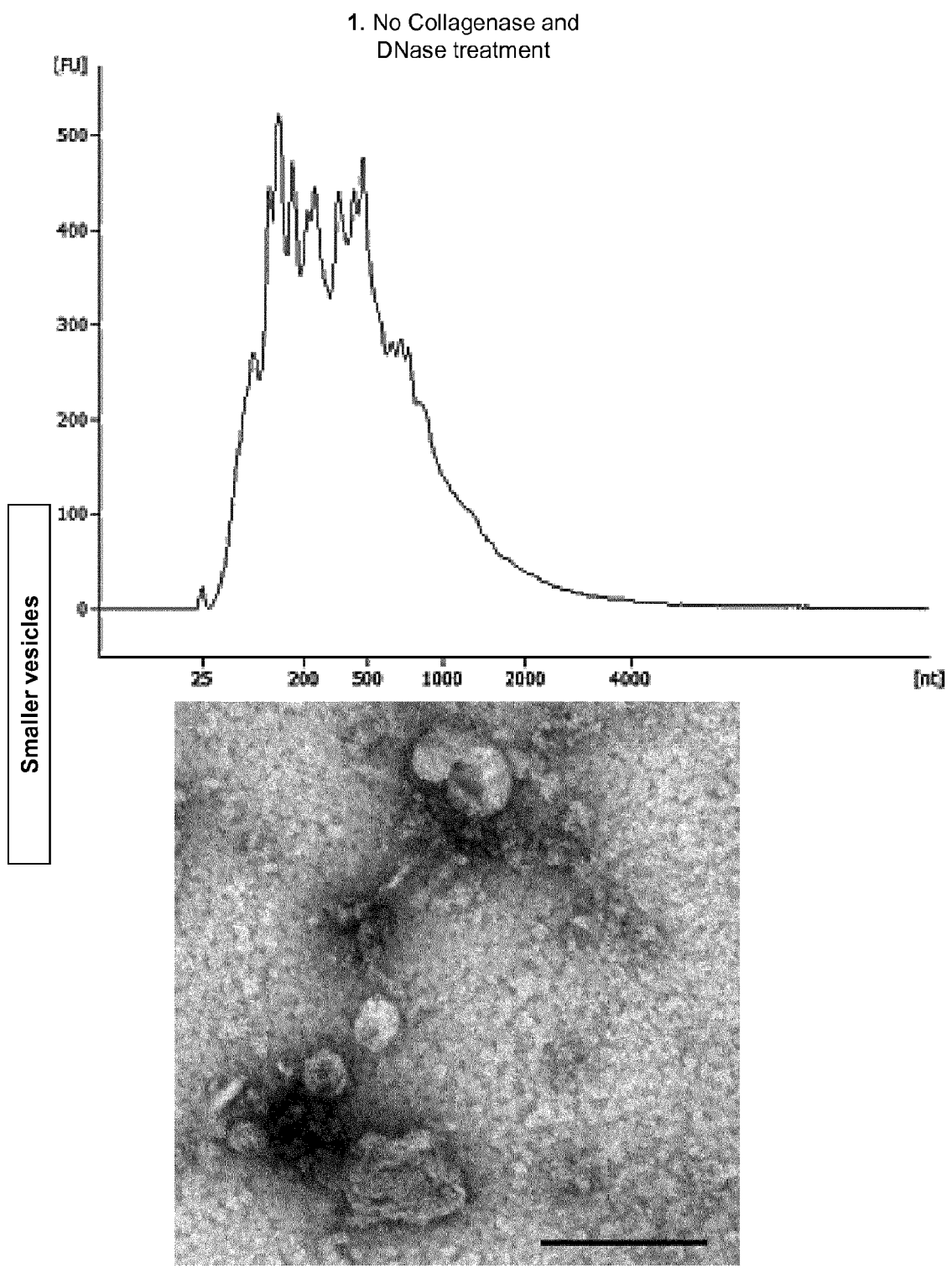
Figure 3E:
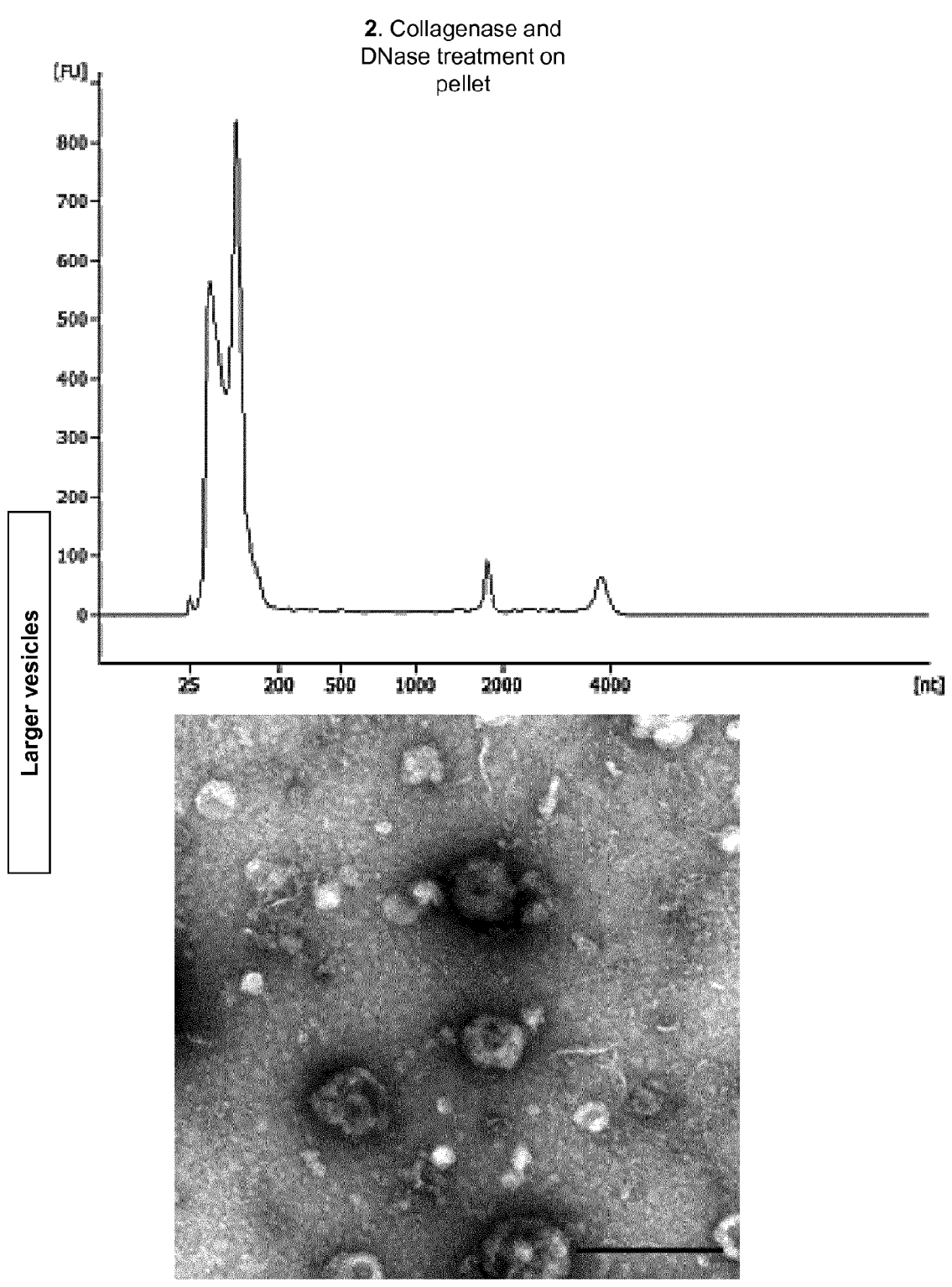
Figure 3F:
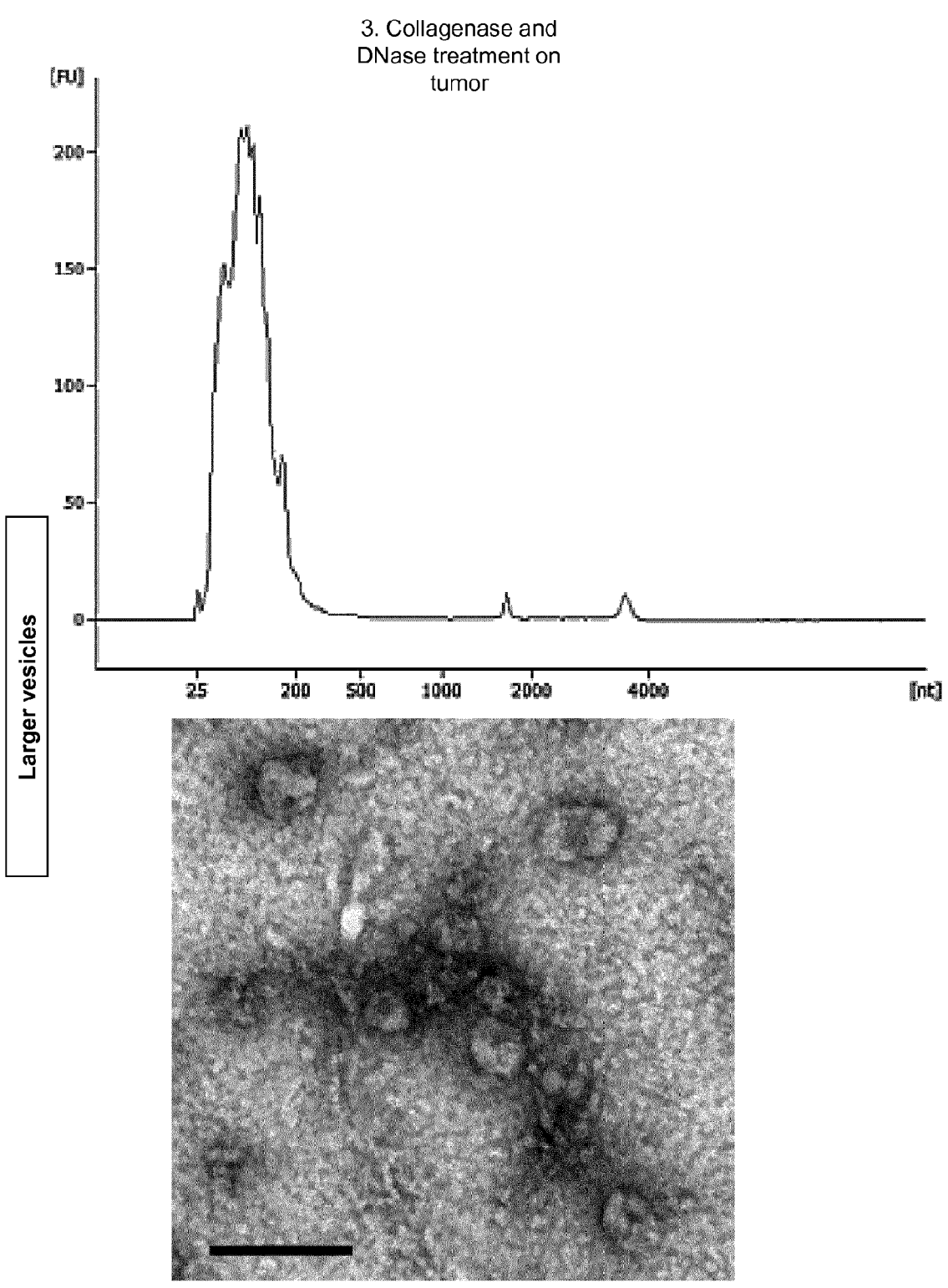

Materials and Method:

A method 200 is provided for isolating extracellular vesicles from melanoma metastatic tissues using centrifugation-based protocols. In the method 200, three slightly different protocols are beneficially employed, and have been tested in practice. As illustrated in FIG. 2, the method 200 starts at step 202. At the step 202, human tissues are obtained from tumor or diseased tissues.

Protocol-1: Two tumor pieces are treatable by employing the protocol 1, to isolate extracellular vesicles. In the protocol-1, the tumor pieces are gently sliced into small fragments (1-2 mm) 204. At step 206, the plurality of pieces of the human tissue is incubated at 37° C. Thereafter, after a filtration step (70 μm pore size), cells and tissue debris are eliminated by centrifugation at 300×g for 10 min and 2000×g for 20 min, as step 210. Supernatant are centrifuged at 16,500×g for 20 min, as step 212, and 110,000×g for 2.5 h, as step 214, to collect larger vesicles and smaller vesicles, respectively; such centrifugation is achieved using, for example, a Ti45 rotor: fixed angle rotor. At step 216, all centrifugations are beneficially performed at a temperature of 4° C. Moreover, in the protocol 1, pellets are beneficially re-suspended in PBS.

Protocol-2: After extracellular vesicle isolation is achieved using the protocol 1, the protocol 2 includes incubating the pellet of larger and smaller vesicles after final ultracentrifugation with Collagenase D (Roche) (2 mg/ml) and DNase I (Roche) (40 U/ml) dissolved in RPMI plain medium (Sigma Aldrich) for 30 min at 37° C., as step 220. At step 222 and 224, after enzymatic treatments, the protocol 2 includes centrifuging larger vesicles at 16,500×g for 15 min and smaller vesicles at 117,000×g for 112 min (Ti70 rotor, fixed angle rotor) to remove enzymes and collect the pellets again. Beneficially, all centrifugations are performed at a temperature of 4° C. Moreover, beneficially, the pellets are re-suspended in PBS.

Protocol-3: As illustrated in FIG. 2, the method 200 may further include step 218. At the step 2218, the plurality of pieces of the human tissue is incubated at 37° C., or any other temperature, in presence of collagenase and DNase. Thereafter, at the step 208 the extracellular vesicles are isolated from the incubated chopped pieces of human tissue. This protocol-3 including gently slicing tumor pieces into small fragments (1-2 mm) and immediately thereafter incubating the small fragments with Collagenase D (2 mg/ml) and DNase I (40 U/ml) dissolved in RPMI plain medium (Sigma Aldrich) for 30 min at 37° C. After a filtration step (70 μm pore size), the protocol 3 includes eliminating cells and tissue debris by centrifugation at 300×g for 10 min and 2000×g for 20 min and then collecting larger and smaller vesicles after centrifugation at 16,500×g for 20 min and 110,000×g for 2.5 h respectively; for example, such centrifugation is achieved using a Ti45 rotor: fixed angle rotor. Moreover, all centrifugations are beneficially performed at a temperature of 4° C. Resulting pellets are then re-suspended in PBS.

For negative stain electron microscopy, the protocol 3 includes placing a drop (10 μl) of isolated extracellular vesicles (both larger and smaller vesicles) onto a glow discharged 200-mesh, namely formvar/carbon Cu copper grids for 15 min (Electron Microscopy Sciences, PA, USA) for 5 min. Thereafter, the protocol 3 includes washing vesicles three times in PBS and then fixing them using 2% paraformaldehyde. After three further washes in PBS, the protocol 3 includes fixing the samples in glutaraldehyde 2.5%, thereafter washing multiple times (up to five times) in filtered water and staining using 2% uranyl acetate for 5 min. The protocol 3 then includes obtaining pictures using an electron microscope, for example a digitized LEO 912AB Omega electron microscope (Carl Zeiss SMT) at 120 kV equipped with a Veleta CCD camera (Olympus-SiS).

Using the aforementioned protocol-1, protocol-2 and protocol-3, it is feasible to extract RNA from both larger and smaller vesicles isolated from melanoma metastatic tissues using miRCURY™ RNA Isolation Kit (Exiqon) according to an associated manufacturer's protocol. Thereafter, RNA profiles are analyzed using a capillary electrophoresis system (for example, an Agilent RNA 6000 Nano Kit for larger and smaller vesicles isolated using protocol 1 and Agilent RNA 6000 Pico Kit for larger and smaller vesicles isolated using protocols 2 and 3). In the protocols 1, 2 and 3, samples are beneficially analyzed using, for example, an Agilent 2100 Bioanalyzer machine (Agilent Technologies).

Results:

Regardless of which of the aforementioned protocols are employed, extracellular vesicles thereby obtained are susceptible to showing typical RNA profiles and morphology of extracellular vesicles; such profiles 300 are illustrated in FIG. 3. Larger vesicles that are pelleted at 16,500×g are susceptible, in practice, to having small RNAs as well as 18S and 28S ribosomal RNA peaks, as illustrated in FIG. 3A1 to 3A3, upper panels. This is comparable to a subpopulation of extracellular vesicles, often called microvesicles, which are released by budding of plasma membrane of cells. By contrast, smaller vesicles that are pelleted at 110,000×g are susceptible, in practice, to having small RNAs, but no relatively prominent ribosomal RNA peaks. This is similar to exosomes, a subpopulation of extracellular vesicles that are released through endocytic pathway, as illustrated in FIG. 3B1 to 3B3, upper panels. In addition, electron microscopy pictures having been found to show that larger vesicles are 100-300 nm in diameter, wherein the typical size range of microvesicles, as illustrated in FIG. 3A1 to 3A3, lower panels, and smaller vesicles are 40 nm to 100 nm in diameter, namely akin to the typical size range of exosomes, as illustrated in FIG. 3B1 to 3B3, lower panels. In fact, a result employing the aforementioned protocols shows that enzymatic treatment does not affect molecular characteristics and morphology of extracellular vesicles.

Example 3: Membrane Isolation and Proteomics Analysis of Extracellular Vesicles

Materials and Method

In a method pursuant to the present disclosure, extracellular vesicles from two melanoma metastatic tissues (MeT1 and MeT2) are isolated by employing the aforementioned protocol-2 described in Example 2 above. Additionally, pursuant to the method of Example 3, extracellular vesicles are isolated from three cell lines, MML1 (melanoma cell line), HMC1 (human mast cell line), and MSC (human mesenchymal stem cells). Conditioned media from cell cultures is then harvested and centrifuged at 300×g for 10 min to remove cells. The supernatant is then centrifuged at 2,000×g for 20 min to remove apoptotic bodies and cell debris. Larger and smaller vesicles are then pelleted at 16,500×g for 20 min and at 118,000×g (Type 45 Ti, Beckman Coulter) for 3.5 h. Thereafter, isolated extracellular vesicles are incubated with 100 mM sodium carbonate solution (pH 12) for 1 h at room temperature with rotation being employed. A potassium chloride solution (1 M) is added and further incubation for 1 h is then employed. Thereafter, samples hereby derived are subjected to an OptiPrep density gradient purification, thereafter ultracentrifuged at 178,000×g (SW 41 Ti, Beckman Coulter) for 2 h, and then membranes are collected from an interface between 30% and 10% iodixanol layers associated with such ultracentrifugation.

Thereafter, a proteome of the membrane of extracellular vesicles is identified by employing LC-MS/MS. Briefly, 30 μg of membranes are beneficially lysed with 2% SDS and sonicated. Tryptic digestion of proteins is then beneficially conducted by employing Filter Associated Aided Sample Preparation. Thereafter, digested peptides are analyzed with an OrbiTrap mass spectrometer. Peak lists of MS data are generated from the mass spectrometer and peptides/proteins are identified and quantified using a MaxQuant quantification tool with an Andromeda search engine (version 1.5.2.8). There is thereby obtained quantitative data, namely by way of employing label-free quantification (LFQ) with a minimum of two ratio counts was applied. Moreover, a normalized LFQ intensity is thereby obtainable. Moreover, protein localization information is obtainable by employing Uniprot.

Figure 4:
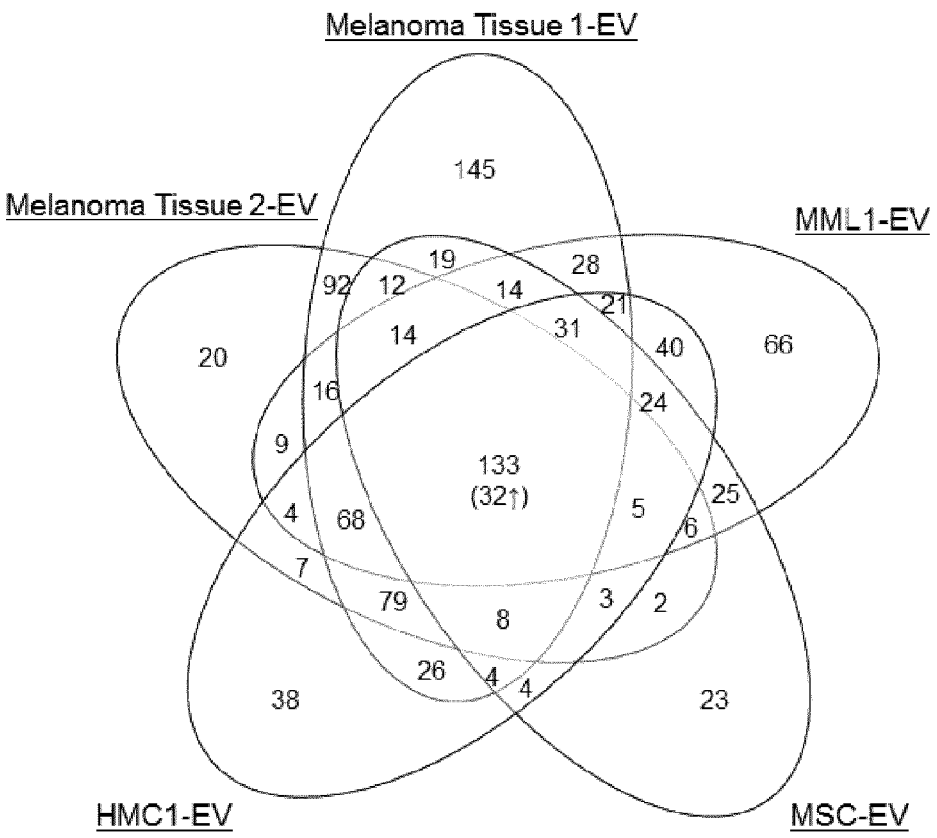
FIG. 4 is a Venn diagram of membrane proteins that are identified from five different extracellular vesicles, two from melanoma metastatic tissues and three from cell lines, by mass spectrometry.
Figure 5:
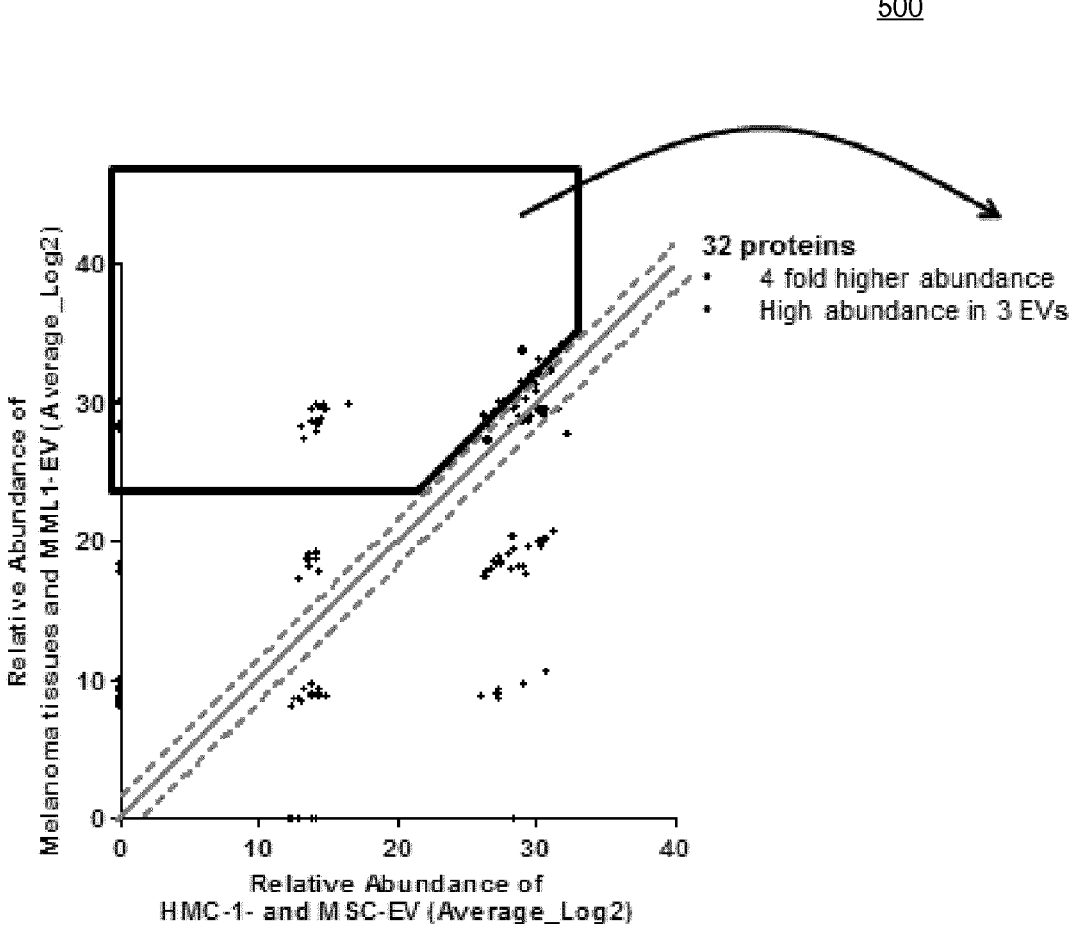
FIG. 5 is an illustration of a relative abundance comparison between membrane proteins from melanoma or non-melanoma-derived extracellular vesicles.
Figures 6A, 6B, 6C, 6D, 6E, 6F:
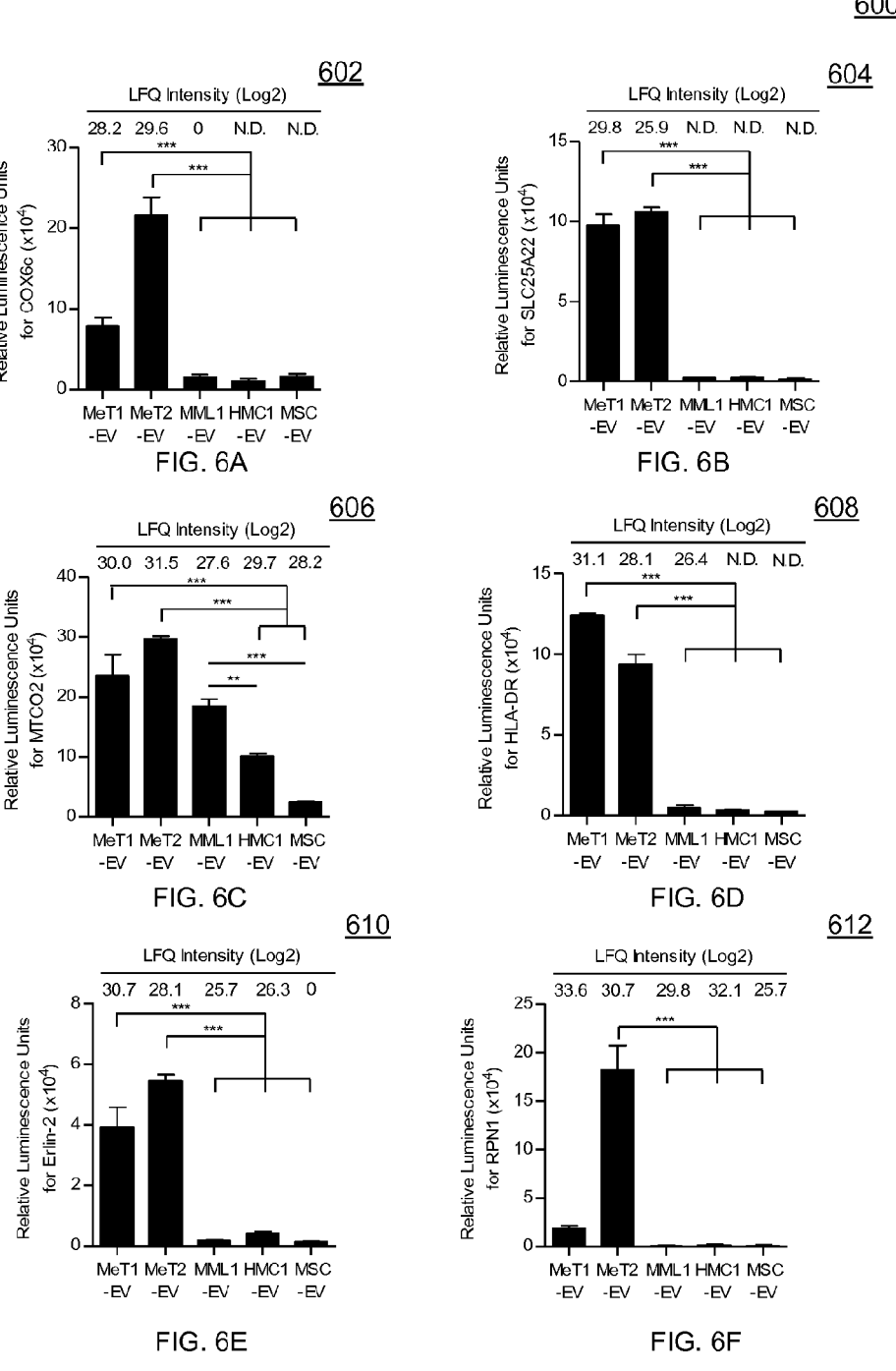
FIGS. 6A-6F provide an illustration of detection of cancer specific membrane proteins on isolated extracellular vesicles by ELISA.

Results:

The method of Example 3 is capable of providing example results, as will next be described. For example, in total, 1239, 901, 1451, 1410, and 959 proteins are susceptible to being identified from extracellular vesicles of MeT1, MeT2, MML1, HMC1, and MSCs, respectively. Only membrane proteins that are annotated in the Uniprot database are beneficially selected and compared to determine unique surface protein profiles of different extracellular vesicles, as illustrated in exemplary graphs 602-612 of FIGS. 6A-F, respectively. Sixteen proteins from melanoma-derived extracellular vesicles (MeT1, MeT2, and MML1) and 92 proteins from melanoma metastatic tissue-derived extracellular vesicles (MeT1 and MeT2) are beneficially selected as cancer-specific surface proteins, as they were not detected in the other membrane isolates, as shown in van diagram 400 of FIG. 4. In addition, 32 proteins are beneficially selected among the 133 common proteins, because these proteins are 4-fold higher in abundance in the melanoma-derived extracellular vesicles compared to non-melanoma-derived extracellular vesicles, but are highly expressed in the three melanoma-derived extracellular vesicles, as shown in an exemplary graph 500 of FIG. 5. These results show that melanoma tissue-derived extracellular vesicles have a unique membrane protein profile, and that embodiments of the present disclosure enable such unique membrane protein profiles to be detected and identified.

Example 4: Detection of Cancer Specific Membrane Proteins from Isolated Extracellular Vesicles

Materials and Method

There is provided a method for this Example 4. The method includes coating extracellular vesicles on 96-well plates for an overnight period at a temperature of 4° C. Thereafter, the method includes removing unbound extracellular vesicles, wherein the plates are blocked with 1% BSA in PBS for 1 h and incubated with anti-COX6c (Santa Cruz Biotechnology), anti-SLC25A22 (Santa Cruz Biotechnology), anti-MT-CO2 (Abcam), anti-HLA-DR (Santa Cruz Biotechnology), anti-Erlin-2 (Abcam), or anti-RPN1 (Thermo Fisher Scientific) antibodies for 2 h. After washing, the appropriate secondary antibodies with HRP are added. Thereafter, the method includes initiating the reaction by adding a TMB substrate solution, terminated by 2M H$_2$SO$_4$; the method includes measuring the optical density at an interrogating radiation wavelength of 450 nm.

Results:

For the method of Example 4, results are obtainable, wherein membrane proteins are highly expressed in melanoma metastatic tissue-derived extracellular vesicles compared to cell line-derived extracellular vesicles, with high correlation of the LFQ intensity from mass spectrometry, as illustrated in exemplary graphs 602-612 of FIGS. 6A-F.

Example 5: Development of Sandwich ELISA System to Detect the Double Membrane Proteins on Extracellular Vesicles

Materials and Method

Figure 7:
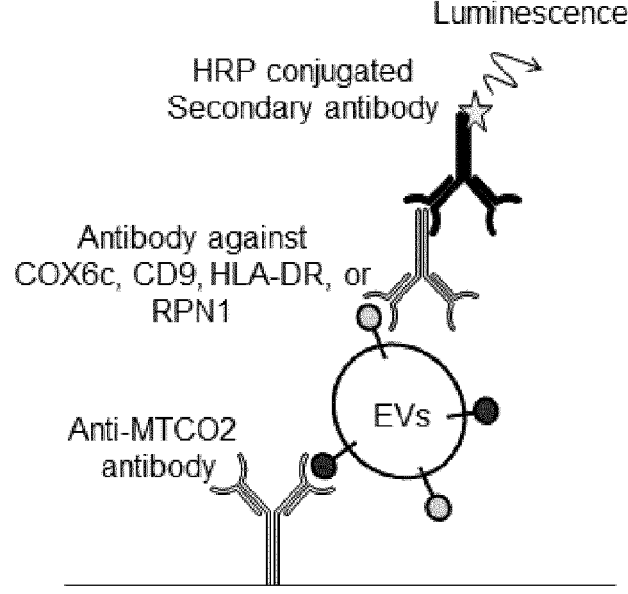
FIG. 7 is a schematic illustration of sandwich ELISA to detect the double membrane proteins on extracellular vesicles.

Overall scheme of sandwich ELISA is described in FIG. 7. MT-CO2 antibody was coated on black 96-well plates for overnight at 4° C. The MT-CO2 antibody was purified on a protein G column prior to use to remove the carrier proteins. The isolated extracellular vesicles were added to the wells and incubated for 2 h at room temperature. After washing with PBS, anti-COX6c, anti-CD9, anti-HLA-DR, or anti-RPN1 antibody was incubated for 1 h and then HRP-conjugated anti-mouse antibody was incubated for 1 h. Luminescent signal was obtained with the BM Chemiluminescence ELISA Substrate (BD Biosciences).

Figures 8A, 8B, 8C, 8D:
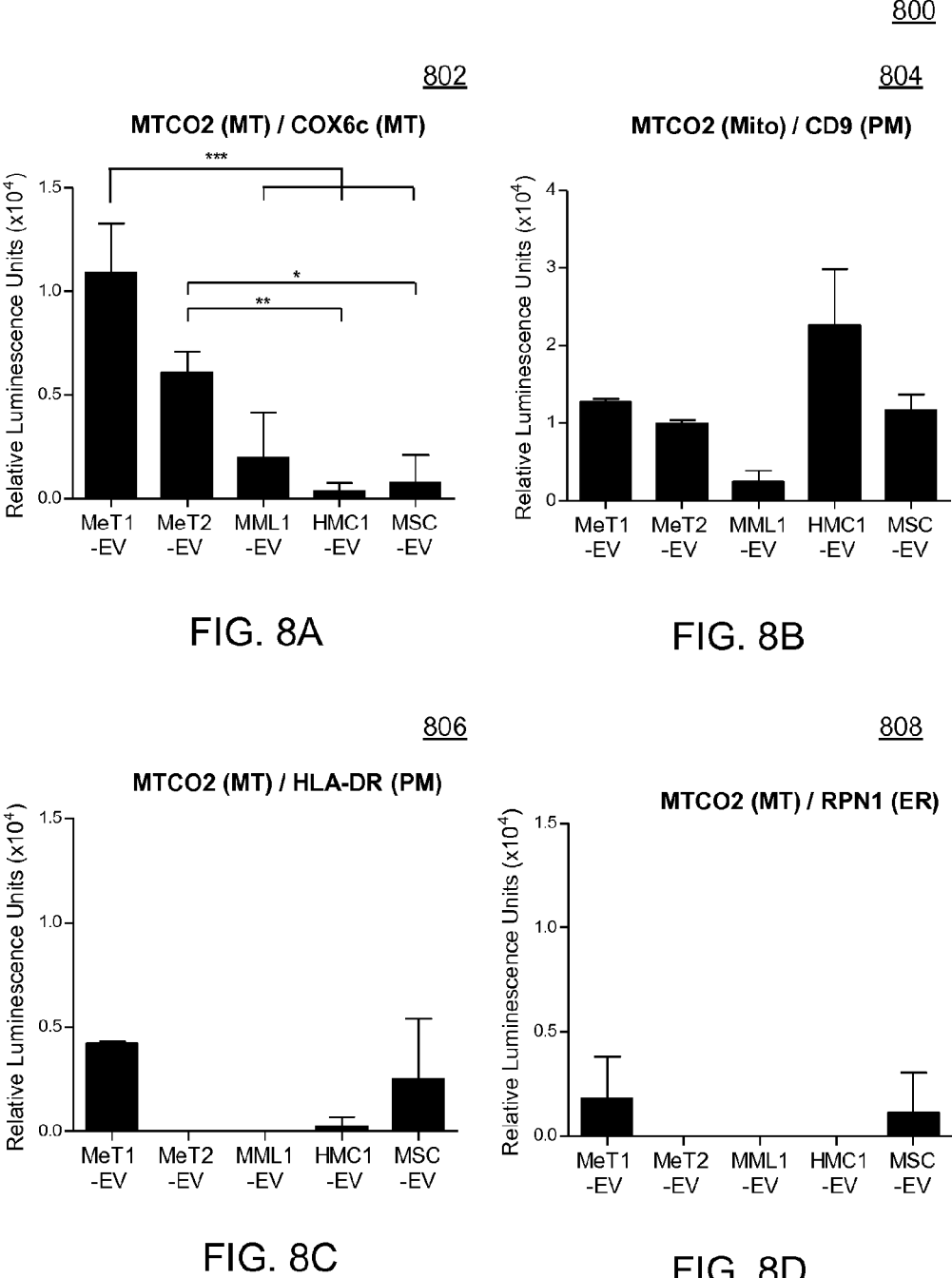
FIGS. 8A-8D provide an illustration of detection of double cancer specific membrane proteins on isolated extracellular vesicles by sandwich ELISA.

Results:

High luminescent signals were observed only in melanoma tissue-derived extracellular vesicles compared with cell line-derived extracellular vesicles when COX6c antibody was used, as shown in an exemplary graph 802 of FIG. 8A. Furthermore, when CD9 antibody was used, high luminescent signals were observed, but there was no difference observed between samples, as shown in an exemplary graph 804 of FIG. 8B. Moreover, high luminescent signals were missing when HLA-DR or RPN1 antibody were used, as shown in exemplary graphs 806, 808 of FIGS. 8C-D. Therefore, based on the FIGS. 8A-D, a conclusion can be made that the extracellular vesicles include different surface molecular profiles, and the system of the present disclosure works efficiently to detect the cancer specific mitochondrial membrane proteins.

Example 6: Detection of Double Membrane Proteins on Extracellular Vesicles from Patient Samples

Materials and Method

In the Example 6, there is provided method including steps as will next be described. The method includes collecting a total of 20 ml of peripheral blood from melanoma patients and healthy controls in EDTA tubes. The method next includes a step of obtaining plasma therefrom by centrifugation at 1880×g for 10 min, followed by a second centrifugation at 2500×g for 10 min. All centrifugations are beneficially performed at a temperature of 4° C.

For example, the method is implemented by collecting blood samples from ovarian cancer patients after anesthesia, but before performing surgery upon the cancer patients. Beneficially, the method includes collecting 6 ml of blood in EDTA vacutainers using standardized procedures, and then centrifuging and directly aliquoting resulting sample material into Eppendorf tubes, followed by steps of frozing and storing the sample material at a temperature of −80° C. within a period in a range of 30 minutes to 60 minutes after withdrawal. Moreover, the method includes collecting ovarian cystic fluids after one or more ovarian cysts are surgically removed and prepared as described above.

In the method, subsequent steps include purifying an MT-CO2 antibody that is purified by a protein G column prior to use to remove the carrier proteins, then coating onto black 96-well plates for an overnight period at a temperature of 4° C. Thereafter, the plasma or cystic fluid are added to the wells and incubated for 2 h at room temperature. Beneficial, a total of 50 μl of blood plasma from patients and 30 μl of cystic fluid plasma is used when implementing the method. After washing with PBS, the method includes incubating a COX6c antibody was incubated for a period of 1 h and then incubating HRP-conjugated anti-mouse antibody for a period of 1 h. Thereafter, the method includes obtaining a luminescent signal by employing a BM Chemiluminescence ELISA Substrate (BD Biosciences).

Figure 9A:
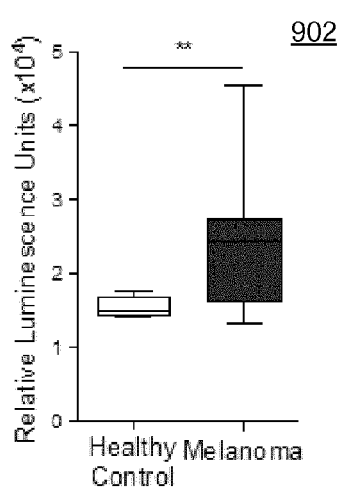
FIGS. 9A-9B provide an illustration of detection of double cancer specific membrane proteins in plasma of melanoma patients and healthy control.
Figure 9B:
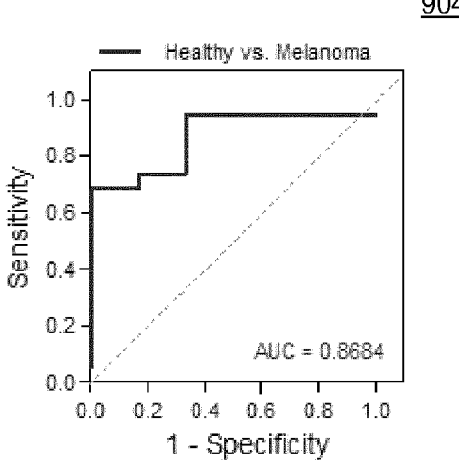
Figure 10A:
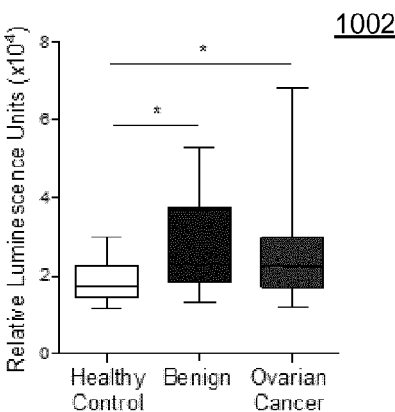
FIGS. 10A-10B provide an illustration of detection of double cancer specific membrane proteins on plasma of ovarian benign control, ovarian cancer patients, and healthy control.
Figure 10B:
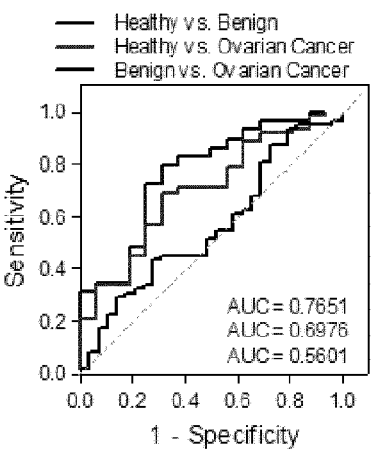
Figure 11A:
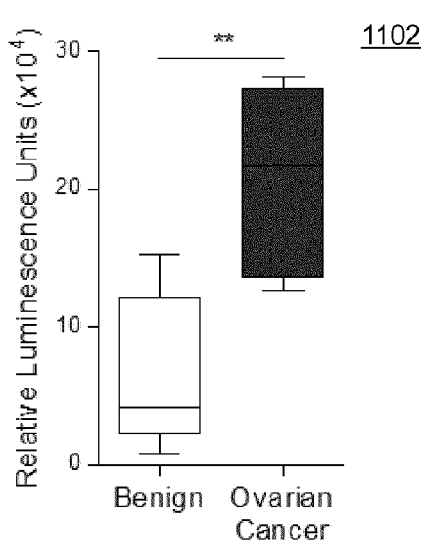
FIGS. 11A-11B provide an illustration of detection of double cancer specific membrane proteins on cystic fluids of ovarian benign control and ovarian cancer patients.
Figure 11B:
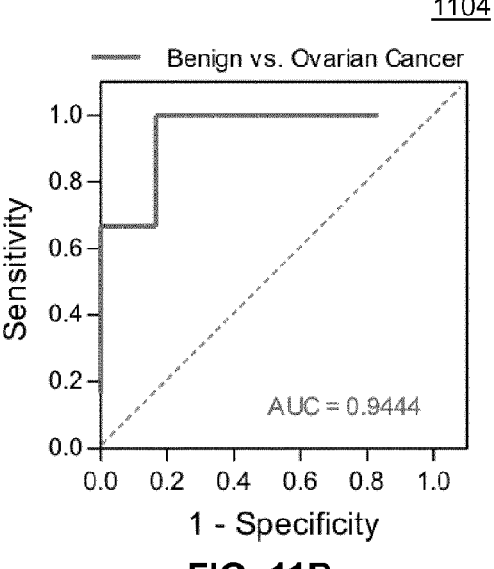

Results:

When employing the method of Example 4, higher levels of combined MT-CO2 and COX6c are susceptible to being detected in plasma of melanoma patients compared with healthy controls as shown in exemplary graph 902 of FIG. 9A with good ROC curve (AUC=0.8684) characteristics as shown in exemplary graph 904 of FIG. 9B. In addition, MT-CO2 and COX6c are susceptible to being detected in the plasma of both patients with benign and malignant ovarian cysts, without significant differences being observed, but the expression level is higher compared with the healthy controls for both groups as shown in exemplary graph 1002 of FIG. 10A with good ROC curve (AUC=0.6976) characteristics as shown in exemplary graph 1004 of FIG. 10B. Importantly, when the MT-CO2/COX6c is quantified in ovarian cystic fluids directly, a significant difference is potentially observed between benign and ovarian cancer cysts as shown in exemplary graph 1102 of FIG. 11A with good ROC curve (AUC=0.9444) characteristics as shown in exemplary graph 1104 of FIG. 11A. These results suggest that cancer specific membrane proteins on extracellular vesicles are released in malignant disease and can be used as valid biomarkers.

Example 7: Detection of the Nucleic Acids Proteins on Extracellular Vesicles Extracellular vesicles have an aqueous, cargo-containing core surrounded by a roughly spherical bilayer membrane. Arrival of the vesicles at a distant site and fusion with targeted cells allows transport of cargo as diverse as nucleic acids (DNA, mRNA, and microRNA), proteins, and lipids, facilitating important cell-cell communications.

Materials and Method

MT-CO2 antibody was coated on black 96-well plates for overnight at 4° C. The MT-CO2 antibody was purified on a protein G column prior to use to remove the membrane proteins. The extraction of the nucleic acids is done through a spin column-based procedure using affinity membrane binding of all extracellular vesicles. The process of extracting nucleic acids from the isolated extracellular vesicles includes pre-filtering the sample to exclude cell-contamination, and loading on the membrane affinity column followed by a brief wash. The bound vesicles are lysed and eluted with QIAzol; the nucleic acid is extracted by addition of chloroform, precipitated by ethanol and further purified by using an RNeasy column. The extracted nucleic acid is washed with PBS, anti-COX6c, anti-CD9, anti-HLA-DR, or anti-RPN1 antibody and was incubated for 1 h and then HRP-conjugated anti-mouse antibody was incubated for 1 h.

Further, to characterize the nucleic acid eluate, 1 μl of the eluate was subjected to the Bioanalyzer RNA 6000 Pico assay according to the manufacturer's instructions. The aligned fluorescence trace data was exported from the instrument's software into a CSV file and plotted using Microsoft Excel.

Results:

High luminescent signals were observed only in melanoma tissue-derived extracellular vesicles compared with cell line-derived extracellular vesicles when COX6c antibody was used. Furthermore, when CD9 antibody was used, high luminescent signals were observed, but there was no difference observed between samples. Moreover, high luminescent signals were missing when HLA-DR or RPN1 antibody were used. Therefore, based on the high luminescent signals nature of nucleic acid present on the extracellular vesicles is identified.

Example 8: Detection of Tissue-Specific Membrane Protein by Using Alpha LISA Donor and Acceptor Beads

Materials and Method

In the Example 8, there is provided method including steps as will next be described. The method includes collecting a total of 20 ml of peripheral blood from melanoma patients in EDTA tubes. The method next includes a step of obtaining plasma therefrom by centrifugation at 1880×g for 10 min, followed by a second centrifugation at 2500×g for 10 min. All centrifugations are beneficially performed at a temperature of 4° C.

For example, the method is implemented by collecting blood samples from ovarian cancer patients. Beneficially, the method includes collecting 6 ml of blood in EDTA vacutainers using standardized procedures, and then centrifuging and directly aliquoting resulting sample material into Eppendorf tubes, followed by steps of frozing and storing the sample material at a temperature of −80° C. within a period in a range of 30 minutes to 60 minutes after withdrawal.

In the method, subsequent steps include purifying an MT-CO2 antibody that is purified by a protein G column prior to use to remove the carrier proteins, then coating onto black 96-well plates for an overnight period at a temperature of 4° C. Thereafter, the plasma or cystic fluid are added to the wells and incubated for 2 h at room temperature. Beneficial, a total of 50 μl of blood plasma from patients and 30 μl of cystic fluid plasma is used when implementing the method. After washing with PBS, the method includes incubating a COX6c antibody was incubated for a period of 1 h and then incubating HRP-conjugated anti-mouse antibody for a period of 1 h. Thereafter, the method includes obtaining a luminescent signal by employing a BM Chemiluminescence ELISA Substrate (BD Biosciences).

Results:

When employing the method of Example 8, higher luminescent signals were observed only in melanoma tissue-derived extracellular vesicles compared with cell line-derived extracellular vesicles when COX6c antibody was used. Furthermore, when CD9 antibody was used, high luminescent signals were observed, but there was no difference observed between samples. Moreover, high luminescent signals were missing when HLA-DR or RPN1 antibody were used. Therefore, based on the higher luminescent signals, a conclusion can be made that the extracellular vesicles include different surface molecular profiles, and the system of the present disclosure works efficiently to detect the cancer specific mitochondrial membrane proteins.

Modifications to embodiments described in the foregoing are possible without departing from the scope of the invention as defined by the accompanying claims. Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

APPENDIX TO THE SPECIFICATION

TABLE 1

| Uniprot ID | Protein name | Gene name | Primary Localization |
|---|---|---|---|
| P05023 | Sodium/potassium-transporting ATPase subunit alpha-1 | ATP1A1 | Cell membrane |
| Q16891 | MICOS complex subunit MIC60 | IMMT | Mitochondrion inner membrane |
| Q07065 | Cytoskeleton-associated protein 4 | CKAP4 | Endoplasmic reticulum membrane |
| Q13423 | NAD(P) transhydrogenase, mitochondrial | NNT | Mitochondrion inner membrane |
| Q9NVI7 | ATPase family AAA domain-containing protein 3A | ATAD3A | Mitochondrion inner membrane |
| P04843 | Dolichyl-diphosphooligosaccharide--protein glycosyltransferase subunit 1 | RPN1 | Endoplasmic reticulum membrane |
| P25705 | ATP synthase subunit alpha, mitochondrial | ATP5A1 | Mitochondrion inner membrane |
| Q9UJS0 | Calcium-binding mitochondrial carrier protein Aralar2 | SLC25A13 | Mitochondrion inner membrane |
| P27824 | Calnexin | CANX | Endoplasmic reticulum membrane |
| Q9Y4W6 | AFG3-like protein 2 | AFG3L2 | Mitochondrion membrane |
| O60313 | Dynamin-like 120 kDa protein, mitochondrial | OPA1 | Mitochondrion inner membrane |
| P16615 | Sarcoplasmic/endoplasmic reticulum calcium ATPase 2 | ATP2A2 | Endoplasmic reticulum membrane |
| Q5T9A4 | ATPase family AAA domain-containing protein 3B | ATAD3B | Mitochondrion inner membrane |
| Q6NUK1 | Calcium-binding mitochondrial carrier protein SCaMC-1 | SLC25A24 | Mitochondrion inner membrane |
| O95202 | LETM1 and EF-hand domain-containing protein 1, mitochondrial | LETM1 | Mitochondrion inner membrane |
| P11717 | Cation-independent mannose-6-phosphate receptor | IGF2R | Lysosome membrane |
| P21796 | Voltage-dependent anion-selective channel protein 1 | VDAC1 | Mitochondrion outer membrane |
| O75746 | Calcium-binding mitochondrial carrier protein Aralar1 | SLC25A12 | Mitochondrion inner membrane |
| P50416 | Carnitine O-palmitoyltransferase 1, liver isoform | CPT1A | Mitochondrion outer membrane |
| Q13724 | Mannosyl-oligosaccharide glucosidase | MOGS | Endoplasmic reticulum membrane |
| Q99623 | Prohibitin-2 | PHB2 | Mitochondrion inner membrane |
| Q07954 | Prolow-density lipoprotein receptor-related protein 1 | LRP1 | Cell membrane |
| Q9UGP8 | Translocation protein SEC63 homolog | SEC63 | Endoplasmic reticulum membrane |
| P02730 | Band 3 anion transport protein | SLC4A1 | Cell membrane |
| Q00610 | Clathrin heavy chain 1 | CLTC | Cytoplasmic vesicle membrane |
| P54886 | Delta-1-pyrroline-5-carboxylate synthase | ALDH18A1 | Mitochondrion inner membrane |
| P20020 | Plasma membrane calcium-transporting ATPase 1 | ATP2B1 | Cell membrane |
| Q9BWM7 | Sideroflexin-3 | SFXN3 | Mitochondrion membrane |
| Q9HDC9 | Adipocyte plasma membrane-associated protein | APMAP | Membrane |
| P00387 | NADH-cytochrome b5 reductase 3 | CYB5R3 | Endoplasmic reticulum membrane |
| Q00325 | Phosphate carrier protein, mitochondrial | SLC25A3 | Mitochondrion inner membrane |
| P35232 | Prohibitin | PHB | Mitochondrion inner membrane |
| P49257 | Protein ERGIC-53 | LMAN1 | Endoplasmic reticulum-Golgi intermediate compartment membrane |
| Q02978 | Mitochondrial 2-oxoglutarate/malate carrier protein | SLC25A11 | Mitochondrion inner membrane |
| Q9H9B4 | Sideroflexin-1 | SFXN1 | Mitochondrion membrane |
| P46977 | Dolichyl-diphosphooligosaccharide--protein glycosyltransferase subunit STT3A | STT3A | Endoplasmic reticulum membrane |
| Q8N766 | ER membrane protein complex subunit 1 | EMC1 | Membrane |
| O94905 | Erlin-2 | ERLIN2 | Endoplasmic reticulum membrane |
| Q14254 | Flotillin-2 | FLOT2 | Cell membrane |
| P05556 | Integrin beta-1 | ITGB1 | Cell membrane |

TABLE 1-continued

| Uniprot ID | Protein name | Gene name | Primary Localization |
|---|---|---|---|
| Q9NTJ5 | Phosphatidylinositide phosphatase SAC1 | SACM1L | Endoplasmic reticulum membrane |
| Q93084 | Sarcoplasmic/endoplasmic reticulum calcium ATPase 3 | ATP2A3 | Nucleus membrane |
| P49748 | Very long-chain specific acyl-CoA dehydrogenase, mitochondrial | ACADVL | Mitochondrion inner membrane |
| P05141 | ADP/ATP translocase 2 | SLC25A5 | Mitochondrion inner membrane |
| P12236 | ADP/ATP translocase 3 | SLC25A6 | Mitochondrion inner membrane |
| P04844 | Dolichyl-diphosphooligosaccharide--protein glycosyltransferase subunit 2 | RPN2 | Endoplasmic reticulum membrane |
| O75477 | Erlin-1 | ERLIN1 | Endoplasmic reticulum membrane |
| O75955 | Flotillin-1 | FLOT1 | Cell membrane |
| Q92896 | Golgi apparatus protein 1 | GLG1 | Golgi apparatus membrane |
| P19367 | Hexokinase-1 | HK1 | Mitochondrion outer membrane |
| P30443 | HLA class I histocompatibility antigen, A-1 alpha chain | HLA-A | Membrane |
| P18463 | HLA class I histocompatibility antigen, B-37 alpha chain | HLA-B | Membrane |
| Q969V3 | Nicalin | NCLN | Endoplasmic reticulum membrane |
| P23634 | Plasma membrane calcium-transporting ATPase 4 | ATP2B4 | Cell membrane |
| P08575 | Receptor-type tyrosine-protein phosphatase C | PTPRC | Membrane |
| Q15005 | Signal peptidase complex subunit 2 | SPCS2 | Microsome membrane |
| Q96PQ0 | VPS10 domain-containing receptor SorCS2 | SORCS2 | Membrane |
| P08195 | 4F2 cell-surface antigen heavy chain | SLC3A2 | Apical cell membrane |
| P32189 | Glycerol kinase | GK | Mitochondrion outer membrane |
| P06756 | Integrin alpha-V | ITGAV | Membrane |
| Q14165 | Malectin | MLEC | Endoplasmic reticulum membrane |
| Q9HD20 | Manganese-transporting ATPase 13A1 | ATP13A1 | Endoplasmic reticulum membrane |
| Q15155 | Nodal modulator 1 | NOMO1 | Membrane |
| Q93050 | V-type proton ATPase 116 kDa subunit a isoform 1 | ATP6V0A1 | Cytoplasmic vesicle membrane |
| Q53H12 | Acylglycerol kinase, mitochondrial | AGK | Mitochondrion membrane |
| P12235 | ADP/ATP translocase 1 | SLC25A4 | Mitochondrion inner membrane |
| Q12797 | Aspartyl/asparaginyl beta-hydroxylase | ASPH | Endoplasmic reticulum membrane |
| O75027 | ATP-binding cassette sub-family B member 7, mitochondrial | ABCB7 | Mitochondrion inner membrane |
| P51572 | B-cell receptor-associated protein 31 | BCAP31 | Endoplasmic reticulum membrane |
| O75844 | CAAX prenyl protease 1 homolog | ZMPSTE24 | Endoplasmic reticulum membrane |
| Q02127 | Dihydroorotate dehydrogenase (quinone), mitochondrial | DHODH | Mitochondrion inner membrane |
| P27105 | Erythrocyte band 7 integral membrane protein | STOM | Cell membrane |
| P04439 | HLA class I histocompatibility antigen, A-3 alpha chain | HLA-A | Membrane |
| P16189 | HLA class I histocompatibility antigen, A-31 alpha chain | HLA-A | Membrane |
| P16190 | HLA class I histocompatibility antigen, A-33 alpha chain | HLA-A | Membrane |
| Q04826 | HLA class I histocompatibility antigen, B-40 alpha chain | HLA-B | Membrane |
| P30481 | HLA class I histocompatibility antigen, B-44 alpha chain | HLA-B | Membrane |
| P30490 | HLA class I histocompatibility antigen, B-52 alpha chain | HLA-B | Membrane |
| P30508 | HLA class I histocompatibility antigen, Cw-12 alpha chain | HLA-C | Membrane |
| Q16853 | Membrane primary amine oxidase | AOC3 | Cell membrane |
| Q9NX63 | MICOS complex subunit MIC19 | CHCHD3 | Mitochondrion inner membrane |
| Q9NZM1 | Myoferlin | MYOF | Cell membrane |
| Q9UH99 | SUN domain-containing protein 2 | SUN2 | Nucleus inner membrane |
| P45880 | Voltage-dependent anion-selective channel protein 2 | VDAC2 | Mitochondrion outer membrane |
| Q96A33 | Coiled-coil domain-containing protein 47 | CCDC47 | Membrane |
| P13073 | Cytochrome c oxidase subunit 4 isoform 1, mitochondrial | COX4I1 | Mitochondrion inner membrane |
| P07099 | Epoxide hydrolase 1 | EPHX1 | Microsome membrane |
| P10321 | HLA class I histocompatibility antigen, Cw-7 alpha chain | HLA-C | Membrane |

TABLE 1-continued

| Uniprot ID | Protein name | Gene name | Primary Localization |
|---|---|---|---|
| Q14108 | Lysosome membrane protein 2 | SCARB2 | Lysosome membrane |
| O00264 | Membrane-associated progesterone receptor component 1 | PGRMC1 | Microsome membrane |
| Q9UBV2 | Protein sel-1 homolog 1 | SEL1L | Endoplasmic reticulum membrane |
| Q9UJZ1 | Stomatin-like protein 2, mitochondrial | STOML2 | Mitochondrion inner membrane |
| P02786 | Transferrin receptor protein 1 | TFRC | Cell membrane |
| O43493 | Trans-Golgi network integral membrane protein 2 | TGOLN2 | Cell membrane |
| Q12907 | Vesicular integral-membrane protein VIP36 | LMAN2 | Endoplasmic reticulum-Golgi intermediate compartment membrane |
| P09543 | 2,3-cyclic-nucleotide 3-phosphodiesterase | CNP | Membrane |
| Q96ER9 | Coiled-coil domain-containing protein 51 | CCDC51 | Membrane |
| P08574 | Cytochrome c1, heme protein, mitochondrial | CYC1 | Mitochondrion inner membrane |
| P39656 | Dolichyl-diphosphooligosaccharide--protein glycosyltransferase 48 kDa subunit | DDOST | Endoplasmic reticulum membrane |
| Q8TCJ2 | Dolichyl-diphosphooligosaccharide--protein glycosyltransferase subunit STT3B | STT3B | Endoplasmic reticulum membrane |
| Q53GQ0 | Estradiol 17-beta-dehydrogenase 12 | HSD17B12 | Endoplasmic reticulum membrane |
| P29992 | Guanine nucleotide-binding protein subunit alpha-11 | GNA11 | Cell membrane |
| P10319 | HLA class I histocompatibility antigen, B-58 alpha chain | HLA-B | Membrane |
| P30498 | HLA class I histocompatibility antigen, B-78 alpha chain | HLA-B | Membrane |
| P13761 | HLA class II histocompatibility antigen, DRB1-7 beta chain | HLA-DRB1 | Cell membrane |
| P05107 | Integrin beta-2 | ITGB2 | Membrane |
| P05106 | Integrin beta-3 | ITGB3 | Cell membrane |
| Q6UXV4 | MICOS complex subunit MIC27 | APOOL | Mitochondrion inner membrane |
| Q9Y276 | Mitochondrial chaperone BCS1 | BCS1L | Mitochondrion inner membrane |
| Q9H936 | Mitochondrial glutamate carrier 1 | SLC25A22 | Mitochondrion inner membrane |
| Q6PIU2 | Neutral cholesterol ester hydrolase 1 | NCEH1 | Membrane |
| P61619 | Protein transport protein Sec61 subunit alpha isoform 1 | SEC61A1 | Endoplasmic reticulum membrane |
| O94901 | SUN domain-containing protein 1 | SUN1 | Nucleus inner membrane |
| Q9HD45 | Transmembrane 9 superfamily member 3 | TM9SF3 | Membrane |
| Q9NZ01 | Very-long-chain enoyl-CoA reductase | TECR | Endoplasmic reticulum membrane |
| Q9Y277 | Voltage-dependent anion-selective channel protein 3 | VDAC3 | Mitochondrion outer membrane |
| O95870 | Abhydrolase domain-containing protein 16A | ABHD16A | Membrane |
| Q8TB61 | Adenosine 3-phospho 5-phosphosulfate transporter 1 | SLC35B2 | Golgi apparatus membrane |
| Q969X5 | Endoplasmic reticulum-Golgi intermediate compartment protein 1 | ERGIC1 | Endoplasmic reticulum membrane |
| O94766 | Galactosylgalactosylxylosylprotein 3-beta-glucuronosyltransferase 3 | B3GAT3 | Golgi apparatus membrane |
| Q9H3K2 | Growth hormone-inducible transmembrane protein | GHITM | Mitochondrion inner membrane |
| P30462 | HLA class I histocompatibility antigen, B-14 alpha chain | HLA-B | Membrane |
| P30466 | HLA class I histocompatibility antigen, B-18 alpha chain | HLA-B | Membrane |
| Q31612 | HLA class I histocompatibility antigen, B-73 alpha chain | HLA-B | Membrane |
| P30501 | HLA class I histocompatibility antigen, Cw-2 alpha chain | HLA-C | Membrane |
| Q30154 | HLA class II histocompatibility antigen, DR beta 5 chain | HLA-DRB5 | Cell membrane |
| P50281 | Matrix metalloproteinase-14 | MMP14 | Membrane |
| P50336 | Protoporphyrinogen oxidase | PPOX | Mitochondrion inner membrane |
| Q15907 | Ras-related protein Rab-11B | RAB11B | Recycling endosome membrane |
| Q92544 | Transmembrane 9 superfamily member 4 | TM9SF4 | Membrane |
| P53007 | Tricarboxylate transport protein, mitochondrial | SLC25A1 | Mitochondrion inner membrane |
| P21589 | 5-nucleotidase | NT5E | Cell membrane |
| Q9NRK6 | ATP-binding cassette sub-family B member 10, mitochondrial | ABCB10 | Mitochondrion inner membrane |
| P80723 | Brain acid soluble protein 1 | BASP1 | Cell membrane |
| O96005 | Cleft lip and palate transmembrane protein 1 | CLPTM1 | Membrane |

TABLE 1-continued

| Uniprot ID | Protein name | Gene name | Primary Localization |
|---|---|---|---|
| P22695 | Cytochrome b-c1 complex subunit 2, mitochondrial | UQCRC2 | Mitochondrion inner membrane |
| P09669 | Cytochrome c oxidase subunit 6C | COX6C | Mitochondrion inner membrane |
| Q7Z2K6 | Endoplasmic reticulum metallopeptidase 1 | ERMP1 | Endoplasmic reticulum membrane |
| P42892 | Endothelin-converting enzyme 1 | ECE1 | Cell membrane |
| P29317 | Ephrin type-A receptor 2 | EPHA2 | Cell membrane |
| P16452 | Erythrocyte membrane protein band 4.2 | EPB42 | Cell membrane |
| P63092 | Guanine nucleotide-binding protein G(s) subunit alpha isoforms short | GNAS | Cell membrane |
| P01911 | HLA class II histocompatibility antigen, DRB1-15 beta chain | HLA-DRB1 | Cell membrane |
| Q08431 | Lactadherin | MFGE8 | Membrane |
| Q9UIQ6 | Leucyl-cystinyl aminopeptidase | LNPEP | Cell membrane |
| Q9H0U3 | Magnesium transporter protein 1 | MAGT1 | Cell membrane |
| Q14728 | Major facilitator superfamily domain-containing protein 10 | MFSD10 | Membrane |
| Q8TCT9 | Minor histocompatibility antigen H13 | HM13 | Endoplasmic reticulum membrane |
| O43772 | Mitochondrial carnitine/acylcarnitine carrier protein | SLC25A20 | Mitochondrion inner membrane |
| Q9Y6C9 | Mitochondrial carrier homolog 2 | MTCH2 | Mitochondrion inner membrane |
| Q92542 | Nicastrin | NCSTN | Membrane |
| P16671 | Platelet glycoprotein 4 | CD36 | Cell membrane |
| P61006 | Ras-related protein Rab-8A | RAB8A | Cell membrane |
| Q9Y512 | Sorting and assembly machinery component 50 homolog | SAMM50 | Mitochondrion outer membrane |
| Q9H3N1 | Thioredoxin-related transmembrane protein 1 | TMX1 | Membrane |
| Q99805 | Transmembrane 9 superfamily member 2 | TM9SF2 | Endosome membrane |
| Q13445 | Transmembrane emp24 domain-containing protein 1 | TMED1 | Cell membrane |
| Q7Z7H5 | Transmembrane emp24 domain-containing protein 4 | TMED4 | Endoplasmic reticulum membrane |
| Q9Y3B3 | Transmembrane emp24 domain-containing protein 7 | TMED7 | Endoplasmic reticulum membrane |
| Q9BVK6 | Transmembrane emp24 domain-containing protein 9 | TMED9 | Endoplasmic reticulum membrane |
| P57088 | Transmembrane protein 33 | TMEM33 | Membrane |
| Q9Y487 | V-type proton ATPase 116 kDa subunit a isoform 2 | ATP6V0A2 | Cell membrane |
| Q13488 | V-type proton ATPase 116 kDa subunit a isoform 3 | TCIRG1 | Membrane |
| Q15904 | V-type proton ATPase subunit S1 | ATP6AP1 | Vacuole membrane |
| P49641 | Alpha-mannosidase 2x | MAN2A2 | Golgi apparatus membrane |
| Q9NW15 | Anoctamin-10 | ANO10 | Cell membrane |
| P35613 | Basigin | BSG | Cell membrane |
| Q9UHQ4 | B-cell receptor-associated protein 29 | BCAP29 | Endoplasmic reticulum membrane |
| Q6KCM7 | Calcium-binding mitochondrial carrier protein SCaMC-2 | SLC25A25 | Mitochondrion inner membrane |
| Q9NPL8 | Complex I assembly factor TIMMDC1, mitochondrial | TIMMDC1 | Mitochondrion membrane |
| O43169 | Cytochrome b5 type B | CYB5B | Mitochondrion outer membrane |
| P31930 | Cytochrome b-c1 complex subunit 1, mitochondrial | UQCRC1 | Mitochondrion inner membrane |
| Q7KZN9 | Cytochrome c oxidase assembly protein COX15 homolog | COX15 | Mitochondrion membrane |
| P20674 | Cytochrome c oxidase subunit 5A, mitochondrial | COX5A | Mitochondrion inner membrane |
| P10606 | Cytochrome c oxidase subunit 5B, mitochondrial | COX5B | Mitochondrion inner membrane |
| Q9Y673 | Dolichyl-phosphate beta-glucosyltransferase | ALG5 | Endoplasmic reticulum membrane |
| Q75T13 | GPI inositol-deacylase | PGAP1 | Endoplasmic reticulum membrane |
| Q92643 | GPI-anchor transamidase | PIGK | Endoplasmic reticulum membrane |
| P04233 | HLA class II histocompatibility antigen gamma chain | CD74 | Cell membrane |
| P56199 | Integrin alpha-1 | ITGA1 | Membrane |
| P26006 | Integrin alpha-3 | ITGA3 | Cell membrane |
| P11117 | Lysosomal acid phosphatase | ACP2 | Lysosome membrane |
| P11279 | Lysosome-associated membrane glycoprotein 1 | LAMP1 | Cell membrane |
| O15173 | Membrane-associated progesterone receptor component 2 | PGRMC2 | Membrane |

TABLE 1-continued

| Uniprot ID | Protein name | Gene name | Primary Localization |
|---|---|---|---|
| Q13505 | Metaxin-1 | MTX1 | Membrane |
| Q9NZJ7 | Mitochondrial carrier homolog 1 | MTCH1 | Mitochondrion inner membrane |
| Q9Y3D7 | Mitochondrial import inner membrane translocase subunit TIM16 | PAM16 | Mitochondrion inner membrane |
| O96008 | Mitochondrial import receptor subunit TOM40 homolog | TOMM40 | Mitochondrion outer membrane |
| Q15070 | Mitochondrial inner membrane protein OXA1L | OXA1L | Mitochondrion inner membrane |
| O96011 | Peroxisomal membrane protein 11B | PEX11B | Peroxisome membrane |
| Q9HBL7 | Plasminogen receptor (KT) | PLGRKT | Cell membrane |
| P16284 | Platelet endothelial cell adhesion molecule | PECAM1 | Cell membrane |
| Q16647 | Prostacyclin synthase | PTGIS | Endoplasmic reticulum membrane |
| O15258 | Protein RER1 | RER1 | Golgi apparatus membrane |
| P61026 | Ras-related protein Rab-10 | RAB10 | Cytoplasmic vesicle membrane |
| P51148 | Ras-related protein Rab-5C | RAB5C | Cell membrane |
| P10301 | Ras-related protein R-Ras | RRAS | Cell membrane |
| Q8TC12 | Retinol dehydrogenase 11 | RDH11 | Endoplasmic reticulum membrane |
| P67812 | Signal peptidase complex catalytic subunit SEC11A | SEC11A | Microsome membrane |
| Q9Y5M8 | Signal recognition particle receptor subunit beta | SRPRB | Endoplasmic reticulum membrane |
| P54709 | Sodium/potassium-transporting ATPase subunit beta-3 | ATP1B3 | Cell membrane |
| P11166 | Solute carrier family 2, facilitated glucose transporter member 1 | SLC2A1 | Cell membrane |
| P31040 | Succinate dehydrogenase [ubiquinone] flavoprotein subunit, mitochondrial | SDHA | Mitochondrion inner membrane |
| O00161 | Synaptosomal-associated protein 23 | SNAP23 | Cell membrane |
| Q99442 | Translocation protein SEC62 | SEC62 | Endoplasmic reticulum membrane |
| P51571 | Translocon-associated protein subunit delta | SSR4 | Endoplasmic reticulum membrane |
| Q6ZXV5 | Transmembrane and TPR repeat-containing protein 3 | TMTC3 | Membrane |
| Q15363 | Transmembrane emp24 domain-containing protein 2 | TMED2 | Cytoplasmic vesicle membrane |
| Q9BVC6 | Transmembrane protein 109 | TMEM109 | Nucleus outer membrane |
| Q6UW68 | Transmembrane protein 205 | TMEM205 | Membrane |
| O75396 | Vesicle-trafficking protein SEC22b | SEC22B | Endoplasmic reticulum membrane |
| Q8TDW0 | Volume-regulated anion channel subunit LRRC8C | LRRC8C | Cell membrane |
| Q6PML9 | Zinc transporter 9 | SLC30A9 | Membrane |
| Q9NUQ2 | 1-acyl-sn-glycerol-3-phosphate acyltransferase epsilon | AGPAT5 | Endoplasmic reticulum membrane |
| Q06136 | 3-ketodihydrosphingosine reductase | KDSR | Endoplasmic reticulum membrane |
| O00400 | Acetyl-coenzyme A transporter 1 | SLC33A1 | Endoplasmic reticulum membrane |
| P26572 | Alpha-1,3-mannosyl-glycoprotein 2-beta-N-acetylglucosaminyltransferase | MGAT1 | Golgi apparatus membrane |
| Q10469 | Alpha-1,6-mannosyl-glycoprotein 2-beta-N-acetylglucosaminyltransferase | MGAT2 | Golgi apparatus membrane |
| Q8NE86 | Calcium uniporter protein, mitochondrial | MCU | Mitochondrion inner membrane |
| P16070 | CD44 antigen | CD44 | Cell membrane |
| P21926 | CD9 antigen | CD9 | Membrane |
| Q9NZ45 | CDGSH iron-sulfur domain-containing protein 1 | CISD1 | Mitochondrion outer membrane |
| Q8N5K1 | CDGSH iron-sulfur domain-containing protein 2 | CISD2 | Endoplasmic reticulum membrane |
| Q9NV96 | Cell cycle control protein 50A | TMEM30A | Membrane |
| P43121 | Cell surface glycoprotein MUC18 | MCAM | Membrane |
| Q96G23 | Ceramide synthase 2 | CERS2 | Nucleus membrane |
| Q96S66 | Chloride channel CLIC-like protein 1 | CLCC1 | Membrane |
| Q96KA5 | Cleft lip and palate transmembrane protein 1-like protein | CLPTM1L | Membrane |
| O94886 | CSC1-like protein 1 | TMEM63A | Lysosome membrane |
| P13498 | Cytochrome b-245 light chain | CYBA | Cell membrane |
| Q6IAN0 | Dehydrogenase/reductase SDR family member 7B | DHRS7B | Endoplasmic reticulum membrane |
| O94923 | D-glucuronyl C5-epimerase | GLCE | Golgi apparatus membrane |
| P61803 | Dolichyl-diphosphooligosaccharide--protein glycosyltransferase subunit DAD1 | DAD1 | Endoplasmic reticulum membrane |
| P49961 | Ectonucleoside triphosphate diphosphohydrolase 1 | ENTPD1 | Membrane |

TABLE 1-continued

| Uniprot ID | Protein name | Gene name | Primary Localization |
|---|---|---|---|
| Q9P0I2 | ER membrane protein complex subunit 3 | EMC3 | Membrane |
| Q9NPA0 | ER membrane protein complex subunit 7 | EMC7 | Membrane |
| A0FGR8 | Extended synaptotagmin-2 | ESYT2 | Cell membrane |
| P36269 | Gamma-glutamyltransferase 5 | GGT5 | Membrane |
| P50440 | Glycine amidinotransferase, mitochondrial | GATM | Mitochondrion inner membrane |
| Q96S52 | GPI transamidase component PIG-S | PIGS | Endoplasmic reticulum membrane |
| Q969N2 | GPI transamidase component PIG-T | PIGT | Endoplasmic reticulum membrane |
| P63244 | Guanine nucleotide-binding protein subunit beta-2-like 1 | GNB2L1 | Cell membrane |
| P30273 | High affinity immunoglobulin epsilon receptor subunit gamma | FCER1G | Cell membrane |
| P13747 | HLA class I histocompatibility antigen, alpha chain E | HLA-E | Membrane |
| P01903 | HLA class II histocompatibility antigen, DR alpha chain | HLA-DRA | Cell membrane |
| Q70UQ0 | Inhibitor of nuclear factor kappa-B kinase-interacting protein | IKBIP | Endoplasmic reticulum membrane |
| P17301 | Integrin alpha-2 | ITGA2 | Membrane |
| P23229 | Integrin alpha-6 | ITGA6 | Cell membrane |
| P05362 | Intercellular adhesion molecule 1 | ICAM1 | Membrane |
| Q6UWP7 | Lysocardiolipin acyltransferase 1 | LCLAT1 | Endoplasmic reticulum membrane |
| Q9BQT8 | Mitochondrial 2-oxodicarboxylate carrier | SLC25A21 | Mitochondrion inner membrane |
| Q9UBX3 | Mitochondrial dicarboxylate carrier | SLC25A10 | Mitochondrion inner membrane |
| Q96DA6 | Mitochondrial import inner membrane translocase subunit TIM14 | DNAJC19 | Mitochondrion inner membrane |
| Q969M1 | Mitochondrial import receptor subunit TOM40B | TOMM40L | Mitochondrion outer membrane |
| Q9Y619 | Mitochondrial ornithine transporter 1 | SLC25A15 | Mitochondrion inner membrane |
| P26038 | Moesin | MSN | Cell membrane |
| Q8N2K0 | Monoacylglycerol lipase ABHD12 | ABHD12 | Membrane |
| Q9P0J0 | NADH dehydrogenase [ubiquinone] 1 alpha subcomplex subunit 13 | NDUFA13 | Mitochondrion inner membrane |
| Q9UHQ9 | NADH-cytochrome b5 reductase 1 | CYB5R1 | Membrane |
| O15118 | Niemann-Pick C1 protein | NPC1 | Late endosome membrane |
| Q9UQ90 | Paraplegin | SPG7 | Mitochondrion membrane |
| O60568 | Procollagen-lysine,2-oxoglutarate 5-dioxygenase 3 | PLOD3 | Rough endoplasmic reticulum membrane |
| Q9HCJ1 | Progressive ankylosis protein homolog | ANKH | Membrane |
| P23219 | Prostaglandin G/H synthase 1 | PTGS1 | Microsome membrane |
| Q96JJ7 | Protein disulfide-isomerase TMX3 | TMX3 | Endoplasmic reticulum membrane |
| Q96A26 | Protein FAM162A | FAM162A | Membrane |
| Q96ND0 | Protein FAM210A | FAM210A | Membrane |
| Q9H0X4 | Protein ITFG3 | ITFG3 | Membrane |
| Q96AA3 | Protein RFT1 homolog | RFT1 | Membrane |
| P63000 | Ras-related C3 botulinum toxin substrate 1 | RAC1 | Cell membrane |
| P61020 | Ras-related protein Rab-5B | RAB5B | Cell membrane |
| P11233 | Ras-related protein Ral-A | RALA | Cell surface |
| P62834 | Ras-related protein Rap-1A | RAP1A | Cell membrane |
| P61224 | Ras-related protein Rap-1b | RAP1B | Cell membrane |
| P61225 | Ras-related protein Rap-2b | RAP2B | Recycling endosome membrane |
| O75787 | Renin receptor | ATP6AP2 | Membrane |
| Q9NY15 | Stabilin-1 | STAB1 | Membrane |
| Q9BX79 | Stimulated by retinoic acid gene 6 protein homolog | STRA6 | Cell membrane |
| Q86WV6 | Stimulator of interferon genes protein | TMEM173 | Endoplasmic reticulum membrane |
| Q15526 | Surfeit locus protein 1 | SURF1 | Mitochondrion inner membrane |
| O15400 | Syntaxin-7 | STX7 | Early endosome membrane |
| O15533 | Tapasin | TAPBP | Endoplasmic reticulum membrane |
| Q9Y320 | Thioredoxin-related transmembrane protein 2 | TMX2 | Membrane |
| P24557 | Thromboxane-A synthase | TBXAS1 | Endoplasmic reticulum membrane |
| Q5JTV8 | Torsin-1A-interacting protein 1 | TOR1AIP1 | Nucleus inner membrane |
| Q15629 | Translocating chain-associated membrane protein 1 | TRAM1 | Endoplasmic reticulum membrane |
| Q9H061 | Transmembrane protein 126A | TMEM126A | Mitochondrion inner membrane |
| Q6PI78 | Transmembrane protein 65 | TMEM65 | Membrane |
| Q9BQA9 | Uncharacterized protein C17orf62 | C17orf62 | Membrane |
| Q96GQ5 | UPF0420 protein C16orf58 | C16orf58 | Membrane |
| Q9P035 | Very-long-chain (3R)-3-hydroxyacyl-CoA dehydratase 3 | PTPLAD1 | Endoplasmic reticulum membrane |

TABLE 1-continued

| Uniprot ID | Protein name | Gene name | Primary Localization |
|---|---|---|---|
| A1L0T0 | Acetolactate synthase-like protein | ILVBL | Membrane |
| P28907 | ADP-ribosyl cyclase/cyclic ADP-ribose hydrolase 1 | CD38 | Membrane |
| P21397 | Amine oxidase [flavin-containing] A | MAOA | Mitochondrion outer membrane |
| P27338 | Amine oxidase [flavin-containing] B | MAOB | Mitochondrion outer membrane |
| O95782 | AP-2 complex subunit alpha-1 | AP2A1 | Cell membrane |
| O94973 | AP-2 complex subunit alpha-2 | AP2A2 | Cell membrane |
| Q13557 | Calcium/calmodulin-dependent protein kinase type II subunit delta | CAMK2D | Cell membrane |
| P20645 | Cation-dependent mannose-6-phosphate receptor | M6PR | Lysosome membrane |
| Q5ZPR3 | CD276 antigen | CD276 | Membrane |
| P08962 | CD63 antigen | CD63 | Cell membrane |
| P48960 | CD97 antigen | CD97 | Cell membrane |
| O14735 | CDP-diacylglycerol--inositol 3-phosphatidyltransferase | CDIPT | Endoplasmic reticulum membrane |
| Q9BT22 | Chitobiosyldiphosphodolichol beta-mannosyltransferase | ALG1 | Endoplasmic reticulum membrane |
| Q5T3F8 | CSC1-like protein 2 | TMEM63B | Membrane |
| Q9GZY4 | Cytochrome c oxidase assembly factor 1 homolog | COA1 | Mitochondrion inner membrane |
| Q5RI15 | Cytochrome c oxidase protein 20 homolog | COX20 | Mitochondrion membrane |
| P00403 | Cytochrome c oxidase subunit 2 | MT-CO2 | Mitochondrion inner membrane |
| O14672 | Disintegrin and metalloproteinase domain-containing protein 10 | ADAM10 | Cell membrane |
| Q9H3Z4 | DnaJ homolog subfamily C member 5 | DNAJC5 | Membrane |
| Q9NX47 | E3 ubiquitin-protein ligase MARCH5 | MARCH5 | Mitochondrion outer membrane |
| Q96K19 | E3 ubiquitin-protein ligase RNF170 | RNF170 | Endoplasmic reticulum membrane |
| Q86TM6 | E3 ubiquitin-protein ligase synoviolin | SYVN1 | Endoplasmic reticulum membrane |
| Q9UKM7 | Endoplasmic reticulum mannosyl-oligosaccharide 1,2-alpha-mannosidase | MAN1B1 | Endoplasmic reticulum membrane |
| Q96RQ1 | Endoplasmic reticulum-Golgi intermediate compartment protein 2 | ERGIC2 | Endoplasmic reticulum-Golgi intermediate compartment membrane |
| Q9Y282 | Endoplasmic reticulum-Golgi intermediate compartment protein 3 | ERGIC3 | Endoplasmic reticulum-Golgi intermediate compartment membrane |
| Q5J8M3 | ER membrane protein complex subunit 4 | EMC4 | Membrane |
| O75063 | Glycosaminoglycan xylosylkinase | FAM20B | Golgi apparatus membrane |
| Q5H8A4 | GPI ethanolamine phosphate transferase 2 | PIGG | Endoplasmic reticulum membrane |
| P59768 | Guanine nucleotide-binding protein G(I)/G(S)/G(O) subunit gamma-2 | GNG2 | Cell membrane |
| P12314 | High affinity immunoglobulin gamma Fc receptor I | FCGR1A | Cell membrane |
| P04440 | HLA class II histocompatibility antigen, DP beta 1 chain | HLA-DPB1 | Cell membrane |
| P01920 | HLA class II histocompatibility antigen, DQ beta 1 chain | HLA-DQB1 | Cell membrane |
| Q14573 | Inositol 1,4,5-trisphosphate receptor type 3 | ITPR3 | Endoplasmic reticulum membrane |
| P08069 | Insulin-like growth factor 1 receptor | IGF1R | Cell membrane |
| P20702 | Integrin alpha-X | ITGAX | Membrane |
| P32942 | Intercellular adhesion molecule 3 | ICAM3 | Membrane |
| Q8NC56 | LEM domain-containing protein 2 | LEMD2 | Nucleus inner membrane |
| Q96AG4 | Leucine-rich repeat-containing protein 59 | LRRC59 | Microsome membrane |
| Q08722 | Leukocyte surface antigen CD47 | CD47 | Cell membrane |
| Q6PCB7 | Long-chain fatty acid transport protein 1 | SLC27A1 | Cell membrane |
| P33121 | Long-chain-fatty-acid--CoA ligase 1 | ACSL1 | Mitochondrion outer membrane |
| O14880 | Microsomal glutathione S-transferase 3 | MGST3 | Endoplasmic reticulum membrane |
| Q9H2D1 | Mitochondrial folate transporter/carrier | SLC25A32 | Mitochondrion inner membrane |
| Q9BVV7 | Mitochondrial import inner membrane translocase subunit Tim21 | TIMM21 | Mitochondrion membrane |
| O14925 | Mitochondrial import inner membrane translocase subunit Tim23 | TIMM23 | Mitochondrion inner membrane |
| O95563 | Mitochondrial pyruvate carrier 2 | MPC2 | Mitochondrion inner membrane |
| P53985 | Monocarboxylate transporter 1 | SLC16A1 | Cell membrane |
| P08571 | Monocyte differentiation antigen CD14 | CD14 | Cell membrane |
| O96000 | NADH dehydrogenase [ubiquinone] 1 beta subcomplex subunit 10 | NDUFB10 | Mitochondrion inner membrane |
| O43674 | NADH dehydrogenase [ubiquinone] 1 beta subcomplex subunit 5, mitochondrial | NDUFB5 | Mitochondrion inner membrane |
| O95169 | NADH dehydrogenase [ubiquinone] 1 beta subcomplex subunit 8, mitochondrial | NDUFB8 | Mitochondrion inner membrane |

TABLE 1-continued

| Uniprot ID | Protein name | Gene name | Primary Localization |
|---|---|---|---|
| Q9Y6M9 | NADH dehydrogenase [ubiquinone] 1 beta subcomplex subunit 9 | NDUFB9 | Mitochondrion inner membrane |
| O95298 | NADH dehydrogenase [ubiquinone] 1 subunit C2 | NDUFC2 | Mitochondrion inner membrane |
| O75306 | NADH dehydrogenase [ubiquinone] iron-sulfur protein 2, mitochondrial | NDUFS2 | Mitochondrion inner membrane |
| O75489 | NADH dehydrogenase [ubiquinone] iron-sulfur protein 3, mitochondrial | NDUFS3 | Mitochondrion inner membrane |
| Q8IY17 | Neuropathy target esterase | PNPLA6 | Endoplasmic reticulum membrane |
| Q9Y639 | Neuroplastin | NPTN | Cell membrane |
| Q8IXM6 | Nurim | NRM | Nucleus inner membrane |
| Q86WC4 | Osteopetrosis-associated transmembrane protein 1 | OSTM1 | Lysosome membrane |
| Q9NYL4 | Peptidyl-prolyl cis-trans isomerase FKBP11 | FKBP11 | Membrane |
| O75915 | PRA1 family protein 3 | ARL6IP5 | Endoplasmic reticulum membrane |
| Q6P4E1 | Protein CASC4 | CASC4 | Membrane |
| Q8N5M9 | Protein jagunal homolog 1 | JAGN1 | Endoplasmic reticulum membrane |
| P60468 | Protein transport protein Sec61 subunit beta | SEC61B | Endoplasmic reticulum membrane |
| P51153 | Ras-related protein Rab-13 | RAB13 | Cell membrane |
| Q15286 | Ras-related protein Rab-35 | RAB35 | Cell membrane |
| P20339 | Ras-related protein Rab-5A | RAB5A | Cell membrane |
| Q92930 | Ras-related protein Rab-8B | RAB8B | Cell membrane |
| Q00765 | Receptor expression-enhancing protein 5 | REEP5 | Membrane |
| Q16799 | Reticulon-1 | RTN1 | Endoplasmic reticulum membrane |
| Q9NQC3 | Reticulon-4 | RTN4 | Endoplasmic reticulum membrane |
| Q9NRX5 | Serine incorporator 1 | SERINC1 | Endoplasmic reticulum membrane |
| O15269 | Serine palmitoyltransferase 1 | SPTLC1 | Endoplasmic reticulum membrane |
| Q96HS1 | Serine/threonine-protein phosphatase PGAM5, mitochondrial | PGAM5 | Mitochondrion outer membrane |
| Q6P4A7 | Sideroflexin-4 | SFXN4 | Mitochondrion inner membrane |
| Q9BY50 | Signal peptidase complex catalytic subunit SEC11C | SEC11C | Microsome membrane |
| Q9Y6A9 | Signal peptidase complex subunit 1 | SPCS1 | Microsome membrane |
| P61009 | Signal peptidase complex subunit 3 | SPCS3 | Microsome membrane |
| P08240 | Signal recognition particle receptor subunit alpha | SRPR | Endoplasmic reticulum membrane |
| P05026 | Sodium/potassium-transporting ATPase subunit beta-1 | ATP1B1 | Cell membrane |
| Q9BSK2 | Solute carrier family 25 member 33 | SLC25A33 | Mitochondrion inner membrane |
| Q8TBP6 | Solute carrier family 25 member 40 | SLC25A40 | Mitochondrion inner membrane |
| Q96H78 | Solute carrier family 25 member 44 | SLC25A44 | Mitochondrion inner membrane |
| Q12846 | Syntaxin-4 | STX4 | Cell membrane |
| Q9H1E5 | Thioredoxin-related transmembrane protein 4 | TMX4 | Membrane |
| P43307 | Translocon-associated protein subunit alpha | SSR1 | Endoplasmic reticulum membrane |
| O15321 | Transmembrane 9 superfamily member 1 | TM9SF1 | Lysosome membrane |
| Q9Y3A6 | Transmembrane emp24 domain-containing protein 5 | TMED5 | Endoplasmic reticulum membrane |
| P17152 | Transmembrane protein 11, mitochondrial | TMEM11 | Mitochondrion inner membrane |
| Q9NX00 | Transmembrane protein 160 | TMEM160 | Membrane |
| Q9UHN6 | Transmembrane protein 2 | TMEM2 | Membrane |
| Q9H330 | Transmembrane protein 245 | TMEM245 | Membrane |
| Q9H3H5 | UDP-N-acetylglucosamine-dolichyl-phosphate N-acetylglucosaminephosphotransferase | DPAGT1 | Endoplasmic reticulum membrane |
| Q96IX5 | Up-regulated during skeletal muscle growth protein 5 | USMG5 | Mitochondrion membrane |
| Q15836 | Vesicle-associated membrane protein 3 | VAMP3 | Membrane |
| Q9P0L0 | Vesicle-associated membrane protein-associated protein A | VAPA | Endoplasmic reticulum membrane |
| Q99943 | 1-acyl-sn-glycerol-3-phosphate acyltransferase alpha | AGPAT1 | Endoplasmic reticulum membrane |
| Q15125 | 3-beta-hydroxysteroid-Delta(8),Delta(7)-isomerase | EBP | Endoplasmic reticulum membrane |
| Q9UBM7 | 7-dehydrocholesterol reductase | DHCR7 | Endoplasmic reticulum membrane |
| Q15041 | ADP-ribosylation factor-like protein 6-interacting protein 1 | ARL6IP1 | Endomembrane system |

TABLE 1-continued

| Uniprot ID | Protein name | Gene name | Primary Localization |
|---|---|---|---|
| Q9NVJ2 | ADP-ribosylation factor-like protein 8B | ARL8B | Late endosome membrane |
| Q9H6U8 | Alpha-1,2-mannosyltransferase ALG9 | ALG9 | Endoplasmic reticulum membrane |
| P15144 | Aminopeptidase N | ANPEP | Cell membrane |
| Q4KMQ2 | Anoctamin-6 | ANO6 | Cell membrane |
| Q03518 | Antigen peptide transporter 1 | TAP1 | Endoplasmic reticulum membrane |
| Q9BUR5 | Apolipoprotein O | APOO | Membrane |
| P20292 | Arachidonate 5-lipoxygenase-activating protein | ALOX5AP | Nucleus membrane |
| Q6DD88 | Atlastin-3 | ATL3 | Endoplasmic reticulum membrane |
| P00846 | ATP synthase subunit a | MT-ATP6 | Mitochondrion inner membrane |
| O94911 | ATP-binding cassette sub-family A member 8 | ABCA8 | Cell membrane |
| P28288 | ATP-binding cassette sub-family D member 3 | ABCD3 | Peroxisome membrane |
| Q16611 | Bcl-2 homologous antagonist/killer | BAK1 | Mitochondrion membrane |
| Q9Y6X5 | Bis(5-adenosyl)-triphosphatase ENPP4 | ENPP4 | Cell membrane |
| P11836 | B-lymphocyte antigen CD20 | MS4A1 | Cell membrane |
| P55290 | Cadherin-13 | CDH13 | Cell membrane |
| Q8NCH0 | Carbohydrate sulfotransferase 14 | CHST14 | Golgi apparatus membrane |
| Q9ULX7 | Carbonic anhydrase 14 | CA14 | Membrane |
| P26678 | Cardiac phospholamban | PLN | Sarcoplasmic reticulum membrane |
| P23786 | Carnitine O-palmitoyltransferase 2, mitochondrial | CPT2 | Mitochondrion inner membrane |
| Q03135 | Caveolin-1 | CAV1 | Golgi apparatus membrane |
| Q9HA82 | Ceramide synthase 4 | CERS4 | Nucleus membrane |
| Q8N5B7 | Ceramide synthase 5 | CERS5 | Nucleus membrane |
| Q9Y6K0 | Choline/ethanolaminephosphotransferase 1 | CEPT1 | Endoplasmic reticulum membrane |
| Q6UVK1 | Chondroitin sulfate proteoglycan 4 | CSPG4 | Apical cell membrane |
| Q96HD1 | Cysteine-rich with EGF-like domain protein 1 | CRELD1 | Membrane |
| Q53TN4 | Cytochrome b reductase 1 | CYBRD1 | Membrane |
| P04839 | Cytochrome b-245 heavy chain | CYBB | Cell membrane |
| O14949 | Cytochrome b-c1 complex subunit 8 | UQCRQ | Mitochondrion inner membrane |
| Q9UDW1 | Cytochrome b-c1 complex subunit 9 | UQCR10 | Mitochondrion inner membrane |
| Q9Y2R0 | Cytochrome c oxidase assembly factor 3 homolog, mitochondrial | COA3 | Mitochondrion inner membrane |
| O00483 | Cytochrome c oxidase subunit NDUFA4 | NDUFA4 | Mitochondrion inner membrane |
| Q6UW02 | Cytochrome P450 20A1 | CYP20A1 | Membrane |
| Q6UVY6 | DBH-like monooxygenase protein 1 | MOXD1 | Endoplasmic reticulum membrane |
| P78536 | Disintegrin and metalloproteinase domain-containing protein 17 | ADAM17 | Membrane |
| Q9NXW2 | DnaJ homolog subfamily B member 12 | DNAJB12 | Membrane |
| Q9Y5T4 | DnaJ homolog subfamily C member 15 | DNAJC15 | Mitochondrion inner membrane |
| Q9Y672 | Dolichyl pyrophosphate Man9GlcNAc2 alpha-1,3-glucosyltransferase | ALG6 | Endoplasmic reticulum membrane |
| Q9BV10 | Dol-P-Man: Man(7)GlcNAc(2)-PP-Dol alpha-1,6-mannosyltransferase | ALG12 | Endoplasmic reticulum membrane |
| P17813 | Endoglin | ENG | Membrane |
| Q99808 | Equilibrative nucleoside transporter 1 | SLC29A1 | Basolateral cell membrane |
| Q5UCC4 | ER membrane protein complex subunit 10 | EMC10 | Membrane |
| O43909 | Exostosin-like 3 | EXTL3 | Endoplasmic reticulum membrane |
| P15311 | Ezrin | EZR | Apical cell membrane |
| P51648 | Fatty aldehyde dehydrogenase | ALDH3A2 | Endoplasmic reticulum membrane |
| Q9Y4F1 | FERM, RhoGEF and pleckstrin domain-containing protein 1 | FARP1 | Cell membrane |
| Q9NXS2 | Glutaminyl-peptide cyclotransferase-like protein | QPCTL | Golgi apparatus membrane |
| P02724 | Glycophorin-A | GYPA | Cell membrane |
| O43292 | Glycosylphosphatidylinositol anchor attachment 1 protein | GPAA1 | Endoplasmic reticulum membrane |
| Q7Z5G4 | Golgin subfamily A member 7 | GOLGA7 | Golgi apparatus membrane |
| Q9UBI6 | Guanine nucleotide-binding protein G(I)/G(S)/G(O) subunit gamma-12 | GNG12 | Cell membrane |
| P51798 | H(+)/Cl(−) exchange transporter 7 | CLCN7 | Lysosome membrane |
| P20036 | HLA class II histocompatibility antigen, DP alpha 1 chain | HLA-DPA1 | Cell membrane |
| P55899 | IgG receptor FcRn large subunit p51 | FCGRT | Cell membrane |
| Q14571 | Inositol 1,4,5-trisphosphate receptor type 2 | ITPR2 | Endoplasmic reticulum membrane |

TABLE 1-continued

| Uniprot ID | Protein name | Gene name | Primary Localization |
|---|---|---|---|
| P08648 | Integrin alpha-5 | ITGA5 | Membrane |
| P08514 | Integrin alpha-IIb | ITGA2B | Membrane |
| P18084 | Integrin beta-5 | ITGB5 | Membrane |
| P13164 | Interferon-induced transmembrane protein 1 | IFITM1 | Cell membrane |
| Q9NPH3 | Interleukin-1 receptor accessory protein | IL1RAP | Cell membrane |
| Q9Y624 | Junctional adhesion molecule A | F11R | Cell junction |
| Q9BX67 | Junctional adhesion molecule C | JAM3 | Cell membrane |
| Q5SVS4 | Kidney mitochondrial carrier protein 1 | SLC25A30 | Mitochondrion inner membrane |
| Q14739 | Lamin-B receptor | LBR | Nucleus inner membrane |
| Q6P1Q0 | LETM1 domain-containing protein 1 | LETMD1 | Mitochondrion outer membrane |
| Q9BU23 | Lipase maturation factor 2 | LMF2 | Endoplasmic reticulum membrane |
| Q6P1M0 | Long-chain fatty acid transport protein 4 | SLC27A4 | Membrane |
| P12318 | Low affinity immunoglobulin gamma Fc region receptor II-a | FCGR2A | Cell membrane |
| P19256 | Lymphocyte function-associated antigen 3 | CD58 | Cell membrane |
| Q6P1A2 | Lysophospholipid acyltransferase 5 | LPCAT3 | Endoplasmic reticulum membrane |
| P21757 | Macrophage scavenger receptor types I and II | MSR1 | Membrane |
| O75352 | Mannose-P-dolichol utilization defect 1 protein | MPDU1 | Membrane |
| Q4ZIN3 | Membralin | TMEM259 | Membrane |
| Q5TGZ0 | MICOS complex subunit MIC10 | MINOS1 | Mitochondrion inner membrane |
| Q8N8R3 | Mitochondrial basic amino acids transporter | SLC25A29 | Mitochondrion inner membrane |
| Q9GZY8 | Mitochondrial fission factor | MFF | Mitochondrion outer membrane |
| Q9UDX5 | Mitochondrial fission process protein 1 | MTFP1 | Mitochondrion inner membrane |
| O43615 | Mitochondrial import inner membrane translocase subunit TIM44 | TIMM44 | Mitochondrion inner membrane |
| Q3ZCQ8 | Mitochondrial import inner membrane translocase subunit TIM50 | TIMM50 | Mitochondrion inner membrane |
| Q9NS69 | Mitochondrial import receptor subunit TOM22 homolog | TOMM22 | Mitochondrion outer membrane |
| Q8N4H5 | Mitochondrial import receptor subunit TOM5 homolog | TOMM5 | Mitochondrion outer membrane |
| Q96B49 | Mitochondrial import receptor subunit TOM6 homolog | TOMM6 | Mitochondrion outer membrane |
| Q9Y5U8 | Mitochondrial pyruvate carrier 1 | MPC1 | Mitochondrion inner membrane |
| Q86Y39 | NADH dehydrogenase [ubiquinone] 1 alpha subcomplex subunit 11 | NDUFA11 | Mitochondrion inner membrane |
| O75438 | NADH dehydrogenase [ubiquinone] 1 beta subcomplex subunit 1 | NDUFB1 | Mitochondrion inner membrane |
| O43676 | NADH dehydrogenase [ubiquinone] 1 beta subcomplex subunit 3 | NDUFB3 | Mitochondrion inner membrane |
| O95168 | NADH dehydrogenase [ubiquinone] 1 beta subcomplex subunit 4 | NDUFB4 | Mitochondrion inner membrane |
| P49821 | NADH dehydrogenase [ubiquinone] flavoprotein 1, mitochondrial | NDUFV1 | Mitochondrion inner membrane |
| P28331 | NADH-ubiquinone oxidoreductase 75 kDa subunit, mitochondrial | NDUFS1 | Mitochondrion inner membrane |
| O95674 | Phosphatidate cytidylyltransferase 2 | CDS2 | Mitochondrion inner membrane |
| P48426 | Phosphatidylinositol 5-phosphate 4-kinase type-2 alpha | PIP4K2A | Cell membrane |
| Q9H490 | Phosphatidylinositol glycan anchor biosynthesis class U protein | PIGU | Endoplasmic reticulum membrane |
| Q2PZI1 | Probable C-mannosyltransferase DPY19L1 | DPY19L1 | Membrane |
| Q6ZPD9 | Probable C-mannosyltransferase DPY19L3 | DPY19L3 | Membrane |
| Q8TED1 | Probable glutathione peroxidase 8 | GPX8 | Membrane |
| Q96KR6 | Protein FAM210B | FAM210B | Membrane |
| Q86UE4 | Protein LYRIC | MTDH | Endoplasmic reticulum membrane |
| P60059 | Protein transport protein Sec61 subunit gamma | SEC61G | Endoplasmic reticulum membrane |
| Q5T9L3 | Protein wntless homolog | WLS | Golgi apparatus membrane |
| Q9GZM5 | Protein YIPF3 | YIPF3 | Cell membrane |
| P35241 | Radixin | RDX | Cell membrane |
| Q9NP72 | Ras-related protein Rab-18 | RAB18 | Cell membrane |
| P61019 | Ras-related protein Rab-2A | RAB2A | Endoplasmic reticulum-Golgi intermediate compartment membrane |
| Q9NRW1 | Ras-related protein Rab-6B | RAB6B | Golgi apparatus membrane |
| P11234 | Ras-related protein Ral-B | RALB | Cell membrane |
| P62070 | Ras-related protein R-Ras2 | RRAS2 | Cell membrane |
| O75298 | Reticulon-2 | RTN2 | Endoplasmic reticulum membrane |

TABLE 1-continued

| Uniprot ID | Protein name | Gene name | Primary Localization |
|---|---|---|---|
| O95197 | Reticulon-3 | RTN3 | Endoplasmic reticulum membrane |
| P84095 | Rho-related GTP-binding protein RhoG | RHOG | Cell membrane |
| Q99720 | Sigma non-opioid intracellular receptor 1 | SIGMAR1 | Nucleus inner membrane |
| Q08357 | Sodium-dependent phosphate transporter 2 | SLC20A2 | Cell membrane |
| Q9UP95 | Solute carrier family 12 member 4 | SLC12A4 | Membrane |
| P11169 | Solute carrier family 2, facilitated glucose transporter member 3 | SLC2A3 | Membrane |
| O15260 | Surfeit locus protein 4 | SURF4 | Endoplasmic reticulum membrane |
| O43760 | Synaptogyrin-2 | SYNGR2 | Membrane |
| Q16563 | Synaptophysin-like protein 1 | SYPL1 | Cytoplasmic vesicle membrane |
| P04216 | Thy-1 membrane glycoprotein | THY1 | Cell membrane |
| P61586 | Transforming protein RhoA | RHOA | Cell membrane |
| P30536 | Translocator protein | TSPO | Mitochondrion membrane |
| Q9UM00 | Transmembrane and coiled-coil domain-containing protein 1 | TMCO1 | Endoplasmic reticulum membrane |
| Q6NXT6 | Transmembrane anterior posterior transformation protein 1 homolog | TAPT1 | Membrane |
| Q14956 | Transmembrane glycoprotein NMB | GPNMB | Cell membrane |
| Q9BXJ8 | Transmembrane protein 120A | TMEM120A | Membrane |
| Q53S58 | Transmembrane protein 177 | TMEM177 | Membrane |
| Q5SNT2 | Transmembrane protein 201 | TMEM201 | Nucleus inner membrane |
| Q9BUB7 | Transmembrane protein 70, mitochondrial | TMEM70 | Mitochondrion inner membrane |
| Q8NBN3 | Transmembrane protein 87A | TMEM87A | Membrane |
| Q9Y275 | Tumor necrosis factor ligand superfamily member 13B | TNFSF13B | Cell membrane |
| Q13454 | Tumor suppressor candidate 3 | TUSC3 | Endoplasmic reticulum membrane |
| Q9NVA1 | Ubiquinol-cytochrome-c reductase complex assembly factor 1 | UQCC1 | Mitochondrion inner membrane |
| Q99807 | Ubiquinone biosynthesis protein COQ7 homolog | COQ7 | Mitochondrion inner membrane |
| Q9Y385 | Ubiquitin-conjugating enzyme E2 J1 | UBE2J1 | Endoplasmic reticulum membrane |
| Q96F25 | UDP-N-acetylglucosamine transferase subunit ALG14 homolog | ALG14 | Endoplasmic reticulum membrane |
| B0I1T2 | Unconventional myosin-Ig | MYO1G | Cell membrane |
| Q6Y1H2 | Very-long-chain (3R)-3-hydroxyacyl-CoA dehydratase 2 | PTPLB | Endoplasmic reticulum membrane |
| Q9UEU0 | Vesicle transport through interaction with t-SNAREs homolog 1B | VTI1B | Late endosome membrane |
| Q9BV40 | Vesicle-associated membrane protein 8 | VAMP8 | Lysosome membrane |
| Q9H0V9 | VIP36-like protein | LMAN2L | Endoplasmic reticulum membrane |
| Q96D96 | Voltage-gated hydrogen channel 1 | HVCN1 | Membrane |
| P61421 | V-type proton ATPase subunit d 1 | ATP6V0D1 | Membrane |
| Q92504 | Zinc transporter SLC39A7 | SLC39A7 | Endoplasmic reticulum membrane |
| Q92604 | Acyl-CoA: lysophosphatidylglycerol acyltransferase 1 | LPGAT1 | Endoplasmic reticulum membrane |
| Q01518 | Adenylyl cyclase-associated protein 1 | CAP1 | Cell membrane |
| P40616 | ADP-ribosylation factor-like protein 1 | ARL1 | Golgi apparatus membrane |
| Q96BM9 | ADP-ribosylation factor-like protein 8A | ARL8A | Late endosome membrane |
| Q16706 | Alpha-mannosidase 2 | MAN2A1 | Golgi apparatus membrane |
| Q02094 | Ammonium transporter Rh type A | RHAG | Membrane |
| Q9Y679 | Ancient ubiquitous protein 1 | AUP1 | Endoplasmic reticulum membrane |
| Q9HCE9 | Anoctamin-8 | ANO8 | Cell membrane |
| P63010 | AP-2 complex subunit beta | AP2B1 | Cell membrane |
| Q96CW1 | AP-2 complex subunit mu | AP2M1 | Cell membrane |
| Q07812 | Apoptosis regulator BAX | BAX | Mitochondrion membrane |
| P10415 | Apoptosis regulator Bcl-2 | BCL2 | Mitochondrion outer membrane |
| P29972 | Aquaporin-1 | AQP1 | Cell membrane |
| P03928 | ATP synthase protein 8 | MT-ATP8 | Mitochondrion membrane |
| Q9BXK5 | Bcl-2-like protein 13 | BCL2L13 | Mitochondrion membrane |
| Q8WY22 | BRI3-binding protein | BRI3BP | Mitochondrion outer membrane |
| P08311 | Cathepsin G | CTSG | Cell surface |
| P48509 | CD151 antigen | CD151 | Membrane |
| P13987 | CD59 glycoprotein | CD59 | Cell membrane |
| P60033 | CD81 antigen | CD81 | Membrane |
| P27701 | CD82 antigen | CD82 | Membrane |
| P14209 | CD99 antigen | CD99 | Membrane |
| P60953 | Cell division control protein 42 homolog | CDC42 | Cell membrane |
| Q6ZMG9 | Ceramide synthase 6 | CERS6 | Nucleus membrane |
| Q8WWI5 | Choline transporter-like protein 1 | SLC44A1 | Cell membrane |
| Q8IWA5 | Choline transporter-like protein 2 | SLC44A2 | Membrane |

TABLE 1-continued

| Uniprot ID | Protein name | Gene name | Primary Localization |
|---|---|---|---|
| Q96FZ5 | CKLF-like MARVEL transmembrane domain-containing protein 7 | CMTM7 | Membrane |
| P08174 | Complement decay-accelerating factor | CD55 | Cell membrane |
| Q9UBG0 | C-type mannose receptor 2 | MRC2 | Membrane |
| O14569 | Cytochrome b561 domain-containing protein 2 | CYB561D2 | Membrane |
| P00414 | Cytochrome c oxidase subunit 3 | MT-CO3 | Mitochondrion inner membrane |
| P15954 | Cytochrome c oxidase subunit 7C, mitochondrial | COX7C | Mitochondrion inner membrane |
| P10176 | Cytochrome c oxidase subunit 8A, mitochondrial | COX8A | Mitochondrion inner membrane |
| Q9BUN8 | Derlin-1 | DERL1 | Endoplasmic reticulum membrane |
| Q9GZP9 | Derlin-2 | DERL2 | Endoplasmic reticulum membrane |
| P15924 | Desmoplakin | DSP | Cell junction |
| Q86YN1 | Dolichyldiphosphatase 1 | DOLPP1 | Endoplasmic reticulum membrane |
| P22413 | Ectonucleotide pyrophosphatase/phosphodiesterase family member 1 | ENPP1 | Cell membrane |
| Q9H4M9 | EH domain-containing protein 1 | EHD1 | Recycling endosome membrane |
| Q16134 | Electron transfer flavoprotein-ubiquinone oxidoreductase, mitochondrial | ETFDH | Mitochondrion inner membrane |
| P50402 | Emerin | EMD | Nucleus inner membrane |
| P24530 | Endothelin B receptor | EDNRB | Cell membrane |
| Q9BV81 | ER membrane protein complex subunit 6 | EMC6 | Membrane |
| Q9H4I9 | Essential MCU regulator, mitochondrial | SMDT1 | Mitochondrion inner membrane |
| Q14802 | FXYD domain-containing ion transport regulator 3 | FXYD3 | Membrane |
| Q96BI3 | Gamma-secretase subunit APH-1A | APH1A | Endoplasmic reticulum membrane |
| Q96A29 | GDP-fucose transporter 1 | SLC35C1 | Golgi apparatus membrane |
| O43826 | Glucose-6-phosphate translocase | SLC37A4 | Endoplasmic reticulum membrane |
| P04921 | Glycophorin-C | GYPC | Cell membrane |
| Q2TAP0 | Golgin subfamily A member 7B | GOLGA7B | Golgi apparatus membrane |
| Q9H3S5 | GPI mannosyltransferase 1 | PIGM | Endoplasmic reticulum membrane |
| P63218 | Guanine nucleotide-binding protein G(I)/G(S)/G(O) subunit gamma-5 | GNG5 | Cell membrane |
| Q14344 | Guanine nucleotide-binding protein subunit alpha-13 | GNA13 | Membrane |
| Q7LGA3 | Heparan sulfate 2-O-sulfotransferase 1 | HS2ST1 | Golgi apparatus membrane |
| Q30201 | Hereditary hemochromatosis protein | HFE | Membrane |
| P52789 | Hexokinase-2 | HK2 | Mitochondrion outer membrane |
| Q9Y241 | HIG1 domain family member 1A, mitochondrial | HIGD1A | Mitochondrion membrane |
| P30825 | High affinity cationic amino acid transporter 1 | SLC7A1 | Cell membrane |
| P17693 | HLA class I histocompatibility antigen, alpha chain G | HLA-G | Membrane |
| P28068 | HLA class II histocompatibility antigen, DM beta chain | HLA-DMB | Late endosome membrane |
| P13765 | HLA class II histocompatibility antigen, DO beta chain | HLA-DOB | Endosome membrane |
| Q96CC6 | Inactive rhomboid protein 1 | RHBDF1 | Endoplasmic reticulum membrane |
| Q9Y2U8 | Inner nuclear membrane protein Man1 | LEMD3 | Nucleus inner membrane |
| Q86V85 | Integral membrane protein GPR180 | GPR180 | Membrane |
| Q9UKX5 | Integrin alpha-11 | ITGA11 | Membrane |
| P18564 | Integrin beta-6 | ITGB6 | Membrane |
| Q8N6L1 | Keratinocyte-associated protein 2 | KRTCAP2 | Endoplasmic reticulum membrane |
| Q8NC54 | Keratinocyte-associated transmembrane protein 2 | KCT2 | Membrane |
| Q9ULH0 | Kinase D-interacting substrate of 220 kDa | KIDINS220 | Membrane |
| Q16850 | Lanosterol 14-alpha demethylase | CYP51A1 | Endoplasmic reticulum membrane |
| P19397 | Leukocyte surface antigen CD53 | CD53 | Cell membrane |
| QI3449 | Limbic system-associated membrane protein | LSAMP | Cell membrane |
| Q96S06 | Lipase maturation factor 1 | LMF1 | Endoplasmic reticulum membrane |
| O95573 | Long-chain-fatty-acid--CoA ligase 3 | ACSL3 | Mitochondrion outer membrane |
| Q92633 | Lysophosphatidic acid receptor 1 | LPAR1 | Cell surface |

TABLE 1-continued

| Uniprot ID | Protein name | Gene name | Primary Localization |
|---|---|---|---|
| Q8NF37 | Lysophosphatidylcholine acyltransferase 1 | LPCAT1 | Endoplasmic reticulum membrane |
| Q7L5N7 | Lysophosphatidylcholine acyltransferase 2 | LPCAT2 | Endoplasmic reticulum membrane |
| Q6ZNC8 | Lysophospholipid acyltransferase 1 | MBOAT1 | Membrane |
| Q96N66 | Lysophospholipid acyltransferase 7 | MBOAT7 | Membrane |
| P13473 | Lysosome-associated membrane glycoprotein 2 | LAMP2 | Cell membrane |
| P84157 | Matrix-remodeling-associated protein 7 | MXRA7 | Membrane |
| Q5JRA6 | Melanoma inhibitory activity protein 3 | MIA3 | Endoplasmic reticulum membrane |
| Q8TBP5 | Membrane protein FAM174A | FAM174A | Membrane |
| Q5EB52 | Mesoderm-specific transcript homolog protein | MEST | Endoplasmic reticulum membrane |
| Q99735 | Microsomal glutathione S-transferase 2 | MGST2 | Endoplasmic reticulum membrane |
| Q9Y584 | Mitochondrial import inner membrane translocase subunit Tim22 | TIMM22 | Mitochondrion inner membrane |
| O94826 | Mitochondrial import receptor subunit TOM70 | TOMM70A | Mitochondrion outer membrane |
| Q96LU5 | Mitochondrial inner membrane protease subunit 1 | IMMP1L | Mitochondrion inner membrane |
| Q9BV23 | Monoacylglycerol lipase ABHD6 | ABHD6 | Membrane |
| O95297 | Myelin protein zero-like protein 1 | MPZL1 | Membrane |
| Q96S97 | Myeloid-associated differentiation marker | MYADM | Membrane |
| O43505 | N-acetyllactosaminide beta-1,3-N-acetylglucosaminyltransferase | B3GNT1 | Golgi apparatus membrane |
| P03905 | NADH-ubiquinone oxidoreductase chain 4 | MT-ND4 | Mitochondrion membrane |
| P03915 | NADH-ubiquinone oxidoreductase chain 5 | MT-ND5 | Mitochondrion inner membrane |
| O14786 | Neuropilin-1 | NRP1 | Cell membrane |
| Q15758 | Neutral amino acid transporter B(0) | SLC1A5 | Cell membrane |
| Q8N9A8 | Nuclear envelope phosphatase-regulatory subunit 1 | CNEP1R1 | Nucleus membrane |
| Q92621 | Nuclear pore complex protein Nup205 | NUP205 | Nucleus membrane |
| Q9Y2C4 | Nuclease EXOG, mitochondrial | EXOG | Mitochondrion inner membrane |
| Q9P0S3 | ORM1-like protein 1 | ORMDL1 | Endoplasmic reticulum membrane |
| Q96BW9 | Phosphatidate cytidylyltransferase, mitochondrial | TAMM41 | Mitochondrion inner membrane |
| Q9BVG9 | Phosphatidylserine synthase 2 | PTDSS2 | Endoplasmic reticulum membrane |
| Q8IV08 | Phospholipase D3 | PLD3 | Endoplasmic reticulum membrane |
| Q9NRY6 | Phospholipid scramblase 3 | PLSCR3 | Mitochondrion membrane |
| P13224 | Platelet glycoprotein Ib beta chain | GP1BB | Membrane |
| P09619 | Platelet-derived growth factor receptor beta | PDGFRB | Cell membrane |
| O00592 | Podocalyxin | PODXL | Apical cell membrane |
| P15151 | Poliovirus receptor | PVR | Cell membrane |
| Q8N2U9 | PQ-loop repeat-containing protein 1 | PQLC1 | Membrane |
| O60831 | PRA1 family protein 2 | PRAF2 | Endosome membrane |
| P49810 | Presenilin-2 | PSEN2 | Endoplasmic reticulum membrane |
| Q9UKR5 | Probable ergosterol biosynthetic protein 28 | C14orf1 | Endoplasmic reticulum membrane |
| Q02809 | Procollagen-lysine,2-oxoglutarate 5-dioxygenase 1 | PLOD1 | Rough endoplasmic reticulum membrane |
| Q9Y284 | Protein Asterix | WDR83OS | Membrane |
| Q9P003 | Protein cornichon homolog 4 | CNIH4 | Membrane |
| Q9UBU6 | Protein FAM8A1 | FAM8A1 | Membrane |
| Q9C0E8 | Protein lunapark | LNP | Endoplasmic reticulum membrane |
| Q9NQG1 | Protein MANBAL | MANBAL | Membrane |
| P06703 | Protein S100-A6 | S100A6 | Nucleus envelope |
| Q8TF72 | Protein Shroom3 | SHROOM3 | Cell junction |
| Q9H2V7 | Protein spinster homolog 1 | SPNS1 | Mitochondrion inner membrane |
| Q14761 | Protein tyrosine phosphatase receptor type C-associated protein | PTPRCAP | Membrane |
| O95070 | Protein YIF1A | YIF1A | Endoplasmic reticulum membrane |
| Q5BJH7 | Protein YIF1B | YIF1B | Membrane |
| Q969M3 | Protein YIPF5 | YIPF5 | Endoplasmic reticulum membrane |
| Q04941 | Proteolipid protein 2 | PLP2 | Membrane |
| A6NKF9 | Putative Golgi pH regulator C | GPR89C | Membrane |
| Q14699 | Raftlin | RFTN1 | Cell membrane |
| P46940 | Ras GTPase-activating-like protein IQGAP1 | IQGAP1 | Cell membrane |

TABLE 1-continued

| Uniprot ID | Protein name | Gene name | Primary Localization |
|---|---|---|---|
| Q9UL25 | Ras-related protein Rab-21 | RAB21 | Endoplasmic reticulum membrane |
| P51159 | Ras-related protein Rab-27A | RAB27A | Membrane |
| Q12913 | Receptor-type tyrosine-protein phosphatase eta | PTPRJ | Cell membrane |
| Q969E2 | Secretory carrier-associated membrane protein 4 | SCAMP4 | Membrane |
| Q15165 | Serum paraoxonase/arylesterase 2 | PON2 | Membrane |
| A6NMB1 | Sialic acid-binding Ig-like lectin 16 | SIGLEC16 | Membrane |
| P0DJ93 | Small integral membrane protein 13 | SMIM13 | Membrane |
| Q8N5G0 | Small integral membrane protein 20 | SMIM20 | Membrane |
| Q8WUM9 | Sodium-dependent phosphate transporter 1 | SLC20A1 | Membrane |
| Q9BXP2 | Solute carrier family 12 member 9 | SLC12A9 | Cell membrane |
| Q96BI1 | Solute carrier family 22 member 18 | SLC22A18 | Apical cell membrane |
| Q96GZ6 | Solute carrier family 41 member 3 | SLC41A3 | Cell membrane |
| Q8NBI5 | Solute carrier family 43 member 3 | SLC43A3 | Membrane |
| O94956 | Solute carrier organic anion transporter family member 2B1 | SLCO2B1 | Cell membrane |
| O95136 | Sphingosine 1-phosphate receptor 2 | S1PR2 | Cell membrane |
| Q15738 | Sterol-4-alpha-carboxylate 3-dehydrogenase, decarboxylating | NSDHL | Endoplasmic reticulum membrane |
| P08842 | Steryl-sulfatase | STS | Endoplasmic reticulum membrane |
| O43759 | Synaptogyrin-1 | SYNGR1 | Membrane |
| P34741 | Syndecan-2 | SDC2 | Membrane |
| Q13190 | Syntaxin-5 | STX5 | Endoplasmic reticulum-Golgi intermediate compartment membrane |
| Q9UNK0 | Syntaxin-8 | STX8 | Membrane |
| O00560 | Syntenin-1 | SDCBP | Cell junction |
| O60637 | Tetraspanin-3 | TSPAN3 | Membrane |
| Q8NFQ8 | Torsin-1A-interacting protein 2 | TOR1AIP2 | Endoplasmic reticulum membrane |
| Q9UNL2 | Translocon-associated protein subunit gamma | SSR3 | Endoplasmic reticulum membrane |
| Q9Y3Q3 | Transmembrane emp24 domain-containing protein 3 | TMED3 | Endoplasmic reticulum-Golgi intermediate compartment membrane |
| Q4V9L6 | Transmembrane protein 119 | TMEM119 | Membrane |
| Q9P0S9 | Transmembrane protein 14C | TMEM14C | Mitochondrion membrane |
| Q9HC07 | Transmembrane protein 165 | TMEM165 | Golgi apparatus membrane |
| Q9P2C4 | Transmembrane protein 181 | TMEM181 | Membrane |
| Q6NUQ4 | Transmembrane protein 214 | TMEM214 | Endoplasmic reticulum membrane |
| Q8N2U0 | Transmembrane protein 256 | TMEM256 | Membrane |
| P61165 | Transmembrane protein 258 | TMEM258 | Membrane |
| Q5BJF2 | Transmembrane protein 97 | TMEM97 | Nucleus membrane |
| Q6ZT21 | Transmembrane protein with metallophosphoesterase domain | TMPPE | Membrane |
| Q8IXB3 | Tumor suppressor candidate 5 | TUSC5 | Membrane |
| Q9ULQ1 | Two pore calcium channel protein 1 | TPCN1 | Lysosome membrane |
| Q8N4L2 | Type 2 phosphatidylinositol 4,5-bisphosphate 4-phosphatase | TMEM55A | Late endosome membrane |
| P07948 | Tyrosine-protein kinase Lyn | LYN | Cell membrane |
| Q969S0 | UDP-xylose and UDP-N-acetylglucosamine transporter | SLC35B4 | Golgi apparatus membrane |
| Q8IYS2 | Uncharacterized protein KIAA2013 | KIAA2013 | Membrane |
| Q13336 | Urea transporter 1 | SLC14A1 | Cell membrane |
| Q3ZAQ7 | Vacuolar ATPase assembly integral membrane protein VMA21 | VMA21 | Endoplasmic reticulum membrane |
| Q96GC9 | Vacuole membrane protein 1 | VMP1 | Endoplasmic reticulum-Golgi intermediate compartment membrane |
| Q9Y3E0 | Vesicle transport protein GOT1B | GOLT1B | Golgi apparatus membrane |
| Q8N0U8 | Vitamin K epoxide reductase complex subunit 1-like protein 1 | VKORC1L1 | Endoplasmic reticulum membrane |
| P54289 | Voltage-dependent calcium channel subunit alpha-2/delta-1 | CACNA2D1 | Membrane |
| Q8WY21 | VPS10 domain-containing receptor SorCS1 | SORCS1 | Membrane |
| P27449 | V-type proton ATPase 16 kDa proteolipid subunit | ATP6V0C | Vacuole membrane |
| Q15043 | Zinc transporter ZIP14 | SLC39A14 | Cell membrane |
| P08865 | 40S ribosomal protein SA | RPSA | Cell membrane |
| P17643 | 5,6-dihydroxyindole-2-carboxylic acid oxidase | TYRP1 | Melanosome membrane |

TABLE 1-continued

| Uniprot ID | Protein name | Gene name | Primary Localization |
|---|---|---|---|
| Q00013 | 55 kDa erythrocyte membrane protein | MPP1 | Membrane |
| O00767 | Acyl-CoA desaturase | SCD | Endoplasmic reticulum membrane |
| P25054 | Adenomatous polyposis coli protein | APC | Cell junction |
| Q10588 | ADP-ribosyl cyclase/cyclic ADP-ribose hydrolase 2 | BST1 | Cell membrane |
| P36405 | ADP-ribosylation factor-like protein 3 | ARL3 | Golgi apparatus membrane |
| P05186 | Alkaline phosphatase, tissue-nonspecific isozyme | ALPL | Cell membrane |
| O00116 | Alkyldihydroxyacetonephosphate synthase, peroxisomal | AGPS | Peroxisome membrane |
| Q9NVD7 | Alpha-parvin | PARVA | Cell junction |
| P54920 | Alpha-soluble NSF attachment protein | NAPA | Membrane |
| P04920 | Anion exchange protein 2 | SLC4A2 | Membrane |
| Q86XL3 | Ankyrin repeat and LEM domain-containing protein 2 | ANKLE2 | Endoplasmic reticulum membrane |
| O75843 | AP-1 complex subunit gamma-like 2 | AP1G2 | Golgi apparatus membrane |
| P53680 | AP-2 complex subunit sigma | AP2S1 | Cell membrane |
| P33897 | ATP-binding cassette sub-family D member 1 | ABCD1 | Peroxisome membrane |
| P50895 | Basal cell adhesion molecule | BCAM | Membrane |
| Q13884 | Beta-1-syntrophin | SNTB1 | Cell membrane |
| Q13425 | Beta-2-syntrophin | SNTB2 | Membrane |
| Q9HBI1 | Beta-parvin | PARVB | Cell junction |
| Q9Y5Z0 | Beta-secretase 2 | BACE2 | Membrane |
| Q5VW32 | BRO1 domain-containing protein BROX | BROX | Membrane |
| Q96CX2 | BTB/POZ domain-containing protein KCTD12 | KCTD12 | Cell junction |
| Q16581 | C3a anaphylatoxin chemotactic receptor | C3AR1 | Cell membrane |
| P55287 | Cadherin-11 | CDH11 | Cell membrane |
| P19022 | Cadherin-2 | CDH2 | Cell membrane |
| P10644 | cAMP-dependent protein kinase type I-alpha regulatory subunit | PRKAR1A | Cell membrane |
| P22748 | Carbonic anhydrase 4 | CA4 | Cell membrane |
| P14384 | Carboxypeptidase M | CPM | Cell membrane |
| P13688 | Carcinoembryonic antigen-related cell adhesion molecule 1 | CEACAM1 | Cell membrane |
| P40199 | Carcinoembryonic antigen-related cell adhesion molecule 6 | CEACAM6 | Cell membrane |
| P31997 | Carcinoembryonic antigen-related cell adhesion molecule 8 | CEACAM8 | Cell membrane |
| Q6YHK3 | CD109 antigen | CD109 | Cell membrane |
| Q13740 | CD166 antigen | ALCAM | Membrane |
| O43633 | Charged multivesicular body protein 2a | CHMP2A | Late endosome membrane |
| Q96FZ7 | Charged multivesicular body protein 6 | CHMP6 | Endomembrane system |
| Q9NY35 | Claudin domain-containing protein 1 | CLDND1 | Membrane |
| Q9UGN4 | CMRF35-like molecule 8 | CD300A | Cell membrane |
| Q9ULV4 | Coronin-1C | CORO1C | Cell membrane |
| P57737 | Coronin-7 | CORO7 | Golgi apparatus membrane |
| P78310 | Coxsackievirus and adenovirus receptor | CXADR | Cell membrane |
| Q9H1C7 | Cysteine-rich and transmembrane domain-containing protein 1 | CYSTM1 | Membrane |
| P14927 | Cytochrome b-c1 complex subunit 7 | UQCRB | Mitochondrion inner membrane |
| P47985 | Cytochrome b-c1 complex subunit Rieske, mitochondrial | UQCRFS1 | Mitochondrion inner membrane |
| O14548 | Cytochrome c oxidase subunit 7A-related protein, mitochondrial | COX7A2L | Mitochondrion inner membrane |
| Q99418 | Cytohesin-2 | CYTH2 | Cell membrane |
| Q9UKG1 | DCC-interacting protein 13-alpha | APPL1 | Early endosome membrane |
| Q92608 | Dedicator of cytokinesis protein 2 | DOCK2 | Endomembrane system |
| Q15392 | Delta(24)-sterol reductase | DHCR24 | Endoplasmic reticulum membrane |
| Q92629 | Delta-sarcoglycan | SGCD | Cell membrane |
| Q02413 | Desmoglein-1 | DSG1 | Cell membrane |
| Q16832 | Discoidin domain-containing receptor 2 | DDR2 | Cell membrane |
| Q96PD2 | Discoidin, CUB and LCCL domain-containing protein 2 | DCBLD2 | Membrane |
| Q12959 | Disks large homolog 1 | DLG1 | Membrane |
| P31689 | DnaJ homolog subfamily A member 1 | DNAJA1 | Membrane |
| O60884 | DnaJ homolog subfamily A member 2 | DNAJA2 | Membrane |
| Q9P2X0 | Dolichol-phosphate mannosyltransferase subunit 3 | DPM3 | Endoplasmic reticulum membrane |
| P11532 | Dystrophin | DMD | Cell membrane |
| Q5T4S7 | E3 ubiquitin-protein ligase UBR4 | UBR4 | Membrane |
| Q9NZN4 | EH domain-containing protein 2 | EHD2 | Cell membrane |
| Q9NZN3 | EH domain-containing protein 3 | EHD3 | Cell membrane |
| Q9H223 | EH domain-containing protein 4 | EHD4 | Cell membrane |

TABLE 1-continued

| Uniprot ID | Protein name | Gene name | Primary Localization |
|---|---|---|---|
| Q9NZ08 | Endoplasmic reticulum aminopeptidase 1 | ERAP1 | Endoplasmic reticulum membrane |
| Q9HCU0 | Endosialin | CD248 | Membrane |
| P29320 | Ephrin type-A receptor 3 | EPHA3 | Cell membrane |
| P54760 | Ephrin type-B receptor 4 | EPHB4 | Cell membrane |
| Q9UBC2 | Epidermal growth factor receptor substrate 15-like 1 | EPS15L1 | Cell membrane |
| Q96HE7 | ERO1-like protein alpha | ERO1L | Endoplasmic reticulum membrane |
| Q9BSJ8 | Extended synaptotagmin-1 | ESYT1 | Endoplasmic reticulum membrane |
| Q8N6M3 | Fat storage-inducing transmembrane protein 2 | FITM2 | Endoplasmic reticulum membrane |
| O95864 | Fatty acid desaturase 2 | FADS2 | Endoplasmic reticulum membrane |
| Q9Y5Y0 | Feline leukemia virus subgroup C receptor-related protein 1 | FLVCR1 | Cell membrane |
| P41440 | Folate transporter 1 | SLC19A1 | Membrane |
| Q7Z2K8 | G protein-regulated inducer of neurite outgrowth 1 | GPRIN1 | Cell membrane |
| Q8TB36 | Ganglioside-induced differentiation-associated protein 1 | GDAP1 | Mitochondrion outer membrane |
| P17302 | Gap junction alpha-1 protein | GJA1 | Cell membrane |
| P36383 | Gap junction gamma-1 protein | GJC1 | Cell membrane |
| P35052 | Glypican-1 | GPC1 | Cell membrane |
| O75487 | Glypican-4 | GPC4 | Cell membrane |
| Q9H4G4 | Golgi-associated plant pathogenesis-related protein 1 | GLIPR2 | Golgi apparatus membrane |
| Q9Y653 | G-protein coupled receptor 56 | GPR56 | Cell membrane |
| Q9NZH0 | G-protein coupled receptor family C group 5 member B | GPRC5B | Cell membrane |
| Q9NQ84 | G-protein coupled receptor family C group 5 member C | GPRC5C | Cell membrane |
| P01112 | GTPase HRas | HRAS | Cell membrane |
| P01111 | GTPase NRas | NRAS | Cell membrane |
| Q14C86 | GTPase-activating protein and VPS9 domain-containing protein 1 | GAPVD1 | Membrane |
| Q15382 | GTP-binding protein Rheb | RHEB | Endomembrane system |
| Q9Y6B6 | GTP-binding protein SAR1b | SAR1B | Endoplasmic reticulum membrane |
| O15431 | High affinity copper uptake protein 1 | SLC31A1 | Cell membrane |
| Q5DX21 | Immunoglobulin superfamily member 11 | IGSF11 | Cell membrane |
| O75054 | Immunoglobulin superfamily member 3 | IGSF3 | Membrane |
| Q969P0 | Immunoglobulin superfamily member 8 | IGSF8 | Cell membrane |
| Q71H61 | Immunoglobulin-like domain-containing receptor 2 | ILDR2 | Endoplasmic reticulum membrane |
| Q13308 | Inactive tyrosine-protein kinase 7 | PTK7 | Membrane |
| Q9Y287 | Integral membrane protein 2B | ITM2B | Golgi apparatus membrane |
| P13612 | Integrin alpha-4 | ITGA4 | Membrane |
| Q13683 | Integrin alpha-7 | ITGA7 | Membrane |
| P53708 | Integrin alpha-8 | ITGA8 | Membrane |
| P20701 | Integrin alpha-L | ITGAL | Membrane |
| P11215 | Integrin alpha-M | ITGAM | Membrane |
| Q13418 | Integrin-linked protein kinase | ILK | Cell junction |
| O15554 | Intermediate conductance calcium-activated potassium channel protein 4 | KCNN4 | Membrane |
| P14923 | Junction plakoglobin | JUP | Cell junction |
| Q96J84 | Kin of IRRE-like protein 1 | KIRREL | Cell membrane |
| P42167 | Lamina-associated polypeptide 2, isoforms beta/gamma | TMPO | Nucleus inner membrane |
| P20700 | Lamin-B1 | LMNB1 | Nucleus inner membrane |
| P40126 | L-dopachrome tautomerase | DCT | Melanosome membrane |
| Q15334 | Lethal(2) giant larvae protein homolog 1 | LLGL1 | Early endosome membrane |
| Q14392 | Leucine-rich repeat-containing protein 32 | LRRC32 | Membrane |
| P11049 | Leukocyte antigen CD37 | CD37 | Membrane |
| P16150 | Leukosialin | SPN | Membrane |
| Q16873 | Leukotriene C4 synthase | LTC4S | Nucleus outer membrane |
| Q08477 | Leukotriene-B(4) omega-hydroxylase 2 | CYP4F3 | Endoplasmic reticulum membrane |
| P48059 | LIM and senescent cell antigen-like-containing domain protein 1 | LIMS1 | Cell junction |
| O43561 | Linker for activation of T-cells family member 1 | LAT | Cell membrane |
| O14494 | Lipid phosphate phosphohydrolase 1 | PPAP2A | Cell membrane |
| Q6ZUX7 | Lipoma HMGIC fusion partner-like 2 protein | LHFPL2 | Membrane |

TABLE 1-continued

| Uniprot ID | Protein name | Gene name | Primary Localization |
|---|---|---|---|
| Q5K4L6 | Long-chain fatty acid transport protein 3 | SLC27A3 | Mitochondrion membrane |
| O60488 | Long-chain-fatty-acid--CoA ligase 4 | ACSL4 | Mitochondrion outer membrane |
| P01130 | Low-density lipoprotein receptor | LDLR | Cell membrane |
| Q7Z4W1 | L-xylulose reductase | DCXR | Membrane |
| Q13571 | Lysosomal-associated transmembrane protein 5 | LAPTM5 | Lysosome membrane |
| Q9NZW5 | MAGUK p55 subfamily member 6 | MPP6 | Membrane |
| Q6NUT3 | Major facilitator superfamily domain-containing protein 12 | MFSD12 | Membrane |
| P04156 | Major prion protein | PRNP | Cell membrane |
| Q9BSK0 | MARVEL domain-containing protein 1 | MARVELD1 | Cell membrane |
| Q8IX19 | Mast cell-expressed membrane protein 1 | MCEMP1 | Membrane |
| P10721 | Mast/stem cell growth factor receptor Kit | KIT | Cell membrane |
| P40967 | Melanocyte protein PMEL | PMEL | Endoplasmic reticulum membrane |
| Q16655 | Melanoma antigen recognized by T-cells 1 | MLANA | Endoplasmic reticulum membrane |
| P08582 | Melanotransferrin | MFI2 | Cell membrane |
| Q658P3 | Metalloreductase STEAP3 | STEAP3 | Endosome membrane |
| Q8N3F8 | MICAL-like protein 1 | MICALL1 | Recycling endosome membrane |
| Q99595 | Mitochondrial import inner membrane translocase subunit Tim17-A | TIMM17A | Mitochondrion inner membrane |
| Q15388 | Mitochondrial import receptor subunit TOM20 homolog | TOMM20 | Mitochondrion outer membrane |
| Q8IXI1 | Mitochondrial Rho GTPase 2 | RHOT2 | Mitochondrion outer membrane |
| O15427 | Monocarboxylate transporter 4 | SLC16A3 | Cell membrane |
| O15403 | Monocarboxylate transporter 7 | SLC16A6 | Cell membrane |
| P33527 | Multidrug resistance-associated protein 1 | ABCC1 | Cell membrane |
| O15439 | Multidrug resistance-associated protein 4 | ABCC4 | Membrane |
| O75970 | Multiple PDZ domain protein | MPDZ | Cell membrane |
| P60201 | Myelin proteolipid protein | PLP1 | Cell membrane |
| Q9UI09 | NADH dehydrogenase [ubiquinone] 1 alpha subcomplex subunit 12 | NDUFA12 | Mitochondrion inner membrane |
| P16435 | NADPH--cytochrome P450 reductase | POR | Endoplasmic reticulum membrane |
| Q9Y2A7 | Nck-associated protein 1 | NCKAP1 | Cell membrane |
| P55160 | Nck-associated protein 1-like | NCKAP1L | Cell membrane |
| Q92692 | Nectin-2 | PVRL2 | Cell membrane |
| P08473 | Neprilysin | MME | Cell membrane |
| Q8NF91 | Nesprin-1 | SYNE1 | Nucleus outer membrane |
| P13591 | Neural cell adhesion molecule 1 | NCAM1 | Cell membrane |
| O15394 | Neural cell adhesion molecule 2 | NCAM2 | Cell membrane |
| Q04721 | Neurogenic locus notch homolog protein 2 | NOTCH2 | Cell membrane |
| Q9UM47 | Neurogenic locus notch homolog protein 3 | NOTCH3 | Cell membrane |
| Q7Z3B1 | Neuronal growth regulator 1 | NEGR1 | Cell membrane |
| O60462 | Neuropilin-2 | NRP2 | Membrane |
| P43007 | Neutral amino acid transporter A | SLC1A4 | Membrane |
| Q8N1F7 | Nuclear pore complex protein Nup93 | NUP93 | Nucleus membrane |
| Q99571 | P2X purinoceptor 4 | P2RX4 | Membrane |
| Q9C0B5 | Palmitoyltransferase ZDHHC5 | ZDHHC5 | Cell membrane |
| O75781 | Paralemmin-1 | PALM | Cell membrane |
| Q96HC4 | PDZ and LIM domain protein 5 | PDLIM5 | Cell junction |
| Q14318 | Peptidyl-prolyl cis-trans isomerase FKBP8 | FKBP8 | Mitochondrion membrane |
| Q99755 | Phosphatidylinositol 4-phosphate 5-kinase type-1 alpha | PIP5K1A | Cell membrane |
| O60331 | Phosphatidylinositol 4-phosphate 5-kinase type-1 gamma | PIP5K1C | Cell membrane |
| O15162 | Phospholipid scramblase 1 | PLSCR1 | Cell membrane |
| Q9H8W4 | Pleckstrin homology domain-containing family F member 2 | PLEKHF2 | Early endosome membrane |
| Q9UIW2 | Plexin-A1 | PLXNA1 | Cell membrane |
| O15031 | Plexin-B2 | PLXNB2 | Cell membrane |
| Q9Y4D7 | Plexin-D1 | PLXND1 | Cell membrane |
| Q6NZI2 | Polymerase I and transcript release factor | PTRF | Membrane |
| Q9H7F0 | Probable cation-transporting ATPase 13A3 | ATP13A3 | Membrane |
| O75340 | Programmed cell death protein 6 | PDCD6 | Nucleus membrane |
| Q9P2B2 | Prostaglandin F2 receptor negative regulator | PTGFRN | Endoplasmic reticulum membrane |
| Q8TCG1 | Protein CIP2A | KIAA1524 | Membrane |
| O60610 | Protein diaphanous homolog 1 | DIAPH1 | Cell membrane |
| Q99497 | Protein DJ-1 | PARK7 | Cell membrane |
| Q14156 | Protein EFR3 homolog A | EFR3A | Cell membrane |
| Q9H8M9 | Protein eva-1 homolog A | EVA1A | Endoplasmic reticulum membrane |
| Q8N5C1 | Protein FAM26E | FAM26E | Membrane |
| Q96RT1 | Protein LAP2 | ERBB2IP | Cell junction |
| Q969X1 | Protein lifeguard 3 | TMBIM1 | Membrane |

TABLE 1-continued

| Uniprot ID | Protein name | Gene name | Primary Localization |
|---|---|---|---|
| Q9NUP9 | Protein lin-7 homolog C | LIN7C | Cell membrane |
| Q14160 | Protein scribble homolog | SCRIB | Cell membrane |
| Q15437 | Protein transport protein Sec23B | SEC23B | Golgi apparatus membrane |
| Q9BSA4 | Protein tweety homolog 2 | TTYH2 | Cell membrane |
| Q9C0H2 | Protein tweety homolog 3 | TTYH3 | Cell membrane |
| O75695 | Protein XRP2 | RP2 | Cell membrane |
| Q96EC8 | Protein YIPF6 | YIPF6 | Membrane |
| Q14517 | Protocadherin Fat 1 | FAT1 | Cell membrane |
| O60245 | Protocadherin-7 | PCDH7 | Cell membrane |
| Q14242 | P-selectin glycoprotein ligand 1 | SELPLG | Membrane |
| A6NGU5 | Putative gamma-glutamyltranspeptidase 3 | GGT3P | Membrane |
| Q14644 | Ras GTPase-activating protein 3 | RASA3 | Cell membrane |
| Q9UL26 | Ras-related protein Rab-22A | RAB22A | Endosome membrane |
| Q9ULC3 | Ras-related protein Rab-23 | RAB23 | Cell membrane |
| O00194 | Ras-related protein Rab-27B | RAB27B | Membrane |
| Q9H082 | Ras-related protein Rab-33B | RAB33B | Golgi apparatus membrane |
| P57729 | Ras-related protein Rab-38 | RAB38 | Cell membrane |
| Q9NP90 | Ras-related protein Rab-9B | RAB9B | Cell membrane |
| Q16827 | Receptor-type tyrosine-protein phosphatase O | PTPRO | Membrane |
| Q8IUW5 | RELT-like protein 1 | RELL1 | Cell membrane |
| Q8NFJ5 | Retinoic acid-induced protein 3 | GPRC5A | Cell membrane |
| Q9Y6N7 | Roundabout homolog 1 | ROBO1 | Membrane |
| Q8WTV0 | Scavenger receptor class B member 1 | SCARB1 | Cell membrane |
| O14828 | Secretory carrier-associated membrane protein 3 | SCAMP3 | Membrane |
| O94804 | Serine/threonine-protein kinase 10 | STK10 | Cell membrane |
| Q7KZI7 | Serine/threonine-protein kinase MARK2 | MARK2 | Cell membrane |
| Q08209 | Serine/threonine-protein phosphatase 2B catalytic subunit alpha isoform | PPP3CA | Cell membrane |
| Q9P0V3 | SH3 domain-binding protein 4 | SH3BP4 | Membrane |
| O43699 | Sialic acid-binding Ig-like lectin 6 | SIGLEC6 | Cell membrane |
| Q9NYZ4 | Sialic acid-binding Ig-like lectin 8 | SIGLEC8 | Membrane |
| Q9UIB8 | SLAM family member 5 | CD84 | Cell membrane |
| O75044 | SLIT-ROBO Rho GTPase-activating protein 2 | SRGAP2 | Cell membrane |
| Q8NHG7 | Small VCP/p97-interacting protein | SVIP | Smooth endoplasmic reticulum membrane |
| P31641 | Sodium- and chloride-dependent taurine transporter | SLC6A6 | Cell membrane |
| Q9Y6M7 | Sodium bicarbonate cotransporter 3 | SLC4A7 | Basolateral cell membrane |
| P19634 | Sodium/hydrogen exchanger 1 | SLC9A1 | Membrane |
| Q96QD8 | Sodium-coupled neutral amino acid transporter 2 | SLC38A2 | Cell membrane |
| Q9Y289 | Sodium-dependent multivitamin transporter | SLC5A6 | Membrane |
| P55011 | Solute carrier family 12 member 2 | SLC12A2 | Membrane |
| Q9UGH3 | Solute carrier family 23 member 2 | SLC23A2 | Cell membrane |
| Q96K37 | Solute carrier family 35 member E1 | SLC35E1 | Membrane |
| Q00796 | Sorbitol dehydrogenase | SORD | Mitochondrion membrane |
| Q99523 | Sortilin | SORT1 | Membrane |
| Q13596 | Sorting nexin-1 | SNX1 | Endosome membrane |
| Q96RF0 | Sorting nexin-18 | SNX18 | Endomembrane system |
| O60749 | Sorting nexin-2 | SNX2 | Early endosome membrane |
| Q96L92 | Sorting nexin-27 | SNX27 | Early endosome membrane |
| Q9Y5X1 | Sorting nexin-9 | SNX9 | Cytoplasmic vesicle membrane |
| Q02318 | Sterol 26-hydroxylase, mitochondrial | CYP27A1 | Mitochondrion membrane |
| P50443 | Sulfate transporter | SLC26A2 | Membrane |
| O95425 | Supervillin | SVIL | Cell membrane |
| Q86Y82 | Syntaxin-12 | STX12 | Endosome membrane |
| Q13277 | Syntaxin-3 | STX3 | Membrane |
| Q9HBL0 | Tensin-1 | TNS1 | Cell surface |
| Q68CZ2 | Tensin-3 | TNS3 | Cell junction |
| Q8NG11 | Tetraspanin-14 | TSPAN14 | Membrane |
| O14817 | Tetraspanin-4 | TSPAN4 | Membrane |
| O60779 | Thiamine transporter 1 | SLC19A2 | Membrane |
| Q07157 | Tight junction protein ZO-1 | TJP1 | Cell membrane |
| Q9UP52 | Transferrin receptor protein 2 | TFR2 | Cell membrane |
| Q9Y5S1 | Transient receptor potential cation channel subfamily V member 2 | TRPV2 | Cell membrane |
| P30408 | Transmembrane 4 L6 family member 1 | TM4SF1 | Membrane |
| Q5U3C3 | Transmembrane protein 164 | TMEM164 | Membrane |
| Q8IY95 | Transmembrane protein 192 | TMEM192 | Lysosome membrane |
| Q8WUH6 | Transmembrane protein 263 | TMEM263 | Membrane |
| Q9BQJ4 | Transmembrane protein 47 | TMEM47 | Membrane |
| Q9NW97 | Transmembrane protein 51 | TMEM51 | Membrane |
| Q9HCN3 | Transmembrane protein 8A | TMEM8A | Membrane |

TABLE 1-continued

| Uniprot ID | Protein name | Gene name | Primary Localization |
|---|---|---|---|
| Q6UWD8 | Transmembrane protein C16orf54 | C16orf54 | Membrane |
| Q13641 | Trophoblast glycoprotein | TPBG | Cell membrane |
| Q9BTW9 | Tubulin-specific chaperone D | TBCD | Cell junction |
| P50591 | Tumor necrosis factor ligand superfamily member 10 | TNFSF10 | Membrane |
| Q92956 | Tumor necrosis factor receptor superfamily member 14 | TNFRSF14 | Membrane |
| P25445 | Tumor necrosis factor receptor superfamily member 6 | FAS | Cell membrane |
| Q6RW13 | Type-1 angiotensin II receptor-associated protein | AGTRAP | Endoplasmic reticulum membrane |
| P23458 | Tyrosine-protein kinase JAK1 | JAK1 | Endomembrane system |
| P43405 | Tyrosine-protein kinase SYK | SYK | Cell membrane |
| Q01973 | Tyrosine-protein kinase transmembrane receptor ROR1 | ROR1 | Membrane |
| P07947 | Tyrosine-protein kinase Yes | YES1 | Cell membrane |
| P18031 | Tyrosine-protein phosphatase non-receptor type 1 | PTPN1 | Endoplasmic reticulum membrane |
| P78324 | Tyrosine-protein phosphatase non-receptor type substrate 1 | SIRPA | Membrane |
| O95164 | Ubiquitin-like protein 3 | UBL3 | Cell membrane |
| Q6ZWK4 | Uncharacterized protein C1orf186 | C1orf186 | Membrane |
| P46939 | Utrophin | UTRN | Cell junction |
| Q9P253 | Vacuolar protein sorting-associated protein 18 homolog | VPS18 | Late endosome membrane |
| Q9UK41 | Vacuolar protein sorting-associated protein 28 homolog | VPS28 | Cell membrane |
| Q9H9H4 | Vacuolar protein sorting-associated protein 37B | VPS37B | Late endosome membrane |
| Q9UN37 | Vacuolar protein sorting-associated protein 4A | VPS4A | Prevacuolar compartment membrane |
| O75351 | Vacuolar protein sorting-associated protein 4B | VPS4B | Prevacuolar compartment membrane |
| O95562 | Vesicle transport protein SFT2B | SFT2D2 | Membrane |
| O95292 | Vesicle-associated membrane protein-associated protein B/C | VAPB | Endoplasmic reticulum membrane |
| P21281 | V-type proton ATPase subunit B, brain isoform | ATP6V1B2 | Endomembrane system |
| Q9Y6M5 | Zinc transporter 1 | SLC30A1 | Cell membrane |
| Q9ULF5 | Zinc transporter ZIP10 | SLC39A10 | Membrane |
| Q13433 | Zinc transporter ZIP6 | SLC39A6 | Cell membrane |

The invention claimed is:

1. A method comprising the steps of:

(a) fragmenting a human tissue into a plurality of pieces;

(b) incubating the plurality of pieces with one or more enzymes, wherein the one or more enzymes are selected from a group of proteases including a matrix metalloproteinase, collagenases, and papain and nucleases including DNase, RNase, and Benzonase, wherein the incubating releases extracellular vesicles from the plurality of pieces, thereby generating a mixture of the extracellular vesicles, the plurality of pieces, and the one or more enzymes;

(c) isolating the extracellular vesicles from the mixture;

(d) treating the extracellular vesicles with an aqueous solution, wherein the aqueous solution has a pH in a range of 9 to 14 to generate membranes;

(e) isolating the membranes; and (f) identifying proteins on the membranes by employing mass spectrometry to identify tissue specific membrane proteins.

2. The method of claim 1, wherein the human tissue comprises diseased tissue.

3. The method of claim 2, wherein the diseased tissue is a tumor.

4. The method of claim 3, wherein the tumor is a lung cancer, larynx cancer, stomach cancer, large intestine/rectal cancer, liver cancer, gallbladder cancer, pancreatic cancer, breast cancer, uterine cervical cancer, prostate cancer, or kidney cancer.

5. The method of claim 3, wherein the tumor is a melanoma, bone cancer, muscle cancer, adipose tissue sarcoma, or mesothelioma.

6. The method of claim 3, wherein the tumor is a neuroma, neuroblastoma, or medulloblastoma.

7. The method of claim 1, wherein the human tissue is liver, brain, kidney, heart, lung, skin, stomach, intestines, lymph nodes, bone marrow, peripheral or central nervous tissue, endocrine glands, adipose tissue or muscles.

8. The method of claim 1, wherein isolating the membranes at the step (e) comprises ultracentrifugation.

9. The method of claim 2, further comprising isolating extracellular vesicles from a diseased human tissue using a specific binder for a diseased tissue-specific membrane proteins identified in step (f) and characterizing at least one of:

i. their disease-specific proteome;

ii. their disease-related RNA cargo; and iii. their disease-related DNA cargo.

10. The method of claim 1, wherein the enzymes comprise collagenase D and DNase I.

11. The method of claim 1, wherein isolating the extracellular vesicles at the step (c) comprises filtration of the mixture to generate a flow-through and centrifugation of the flow-through from the filtration to remove cells and tissue debris and provide a supernatant comprising the extracellular vesicles.

* * * * *